United States Patent [19]
Courtemanche et al.

[11] Patent Number: 5,464,847
[45] Date of Patent: Nov. 7, 1995

[54] BRANCHED ALKYLAMINO DERIVATIVES OF THIAZOLE, PROCESSES FOR PREPARING THEM AND PHARMACEUTICAL COMPOSITIONS CONTAINING THEM

[75] Inventors: Gilles Courtemanche, Saint Martin du Tertre; Claudie Gautier, Paris; Danielle Gully, Saubens; Pierre Roger, Montigny le Bretonneux; Gérard Valette, Lacroix Falgarde; Camille G. Wermuth, Strasbourg, all of France

[73] Assignee: Elf Sanofi, Paris, France

[21] Appl. No.: 80,172

[22] Filed: Jun. 23, 1993

[30] Foreign Application Priority Data

Jun. 24, 1992 [FR] France .................. 92 07736

[51] Int. Cl.⁶ .................. C07D 417/12; A61K 31/425
[52] U.S. Cl. .................. 514/342; 514/370; 546/280; 548/190; 548/193
[58] Field of Search .................. 548/190, 193; 546/280; 514/370, 342

[56] References Cited

U.S. PATENT DOCUMENTS 5,232,921  8/1993  Biziere .................. 548/190

FOREIGN PATENT DOCUMENTS 0283390  9/1988  France .
2022085  12/1979  United Kingdom .
9109857  7/1991  WIPO .

OTHER PUBLICATIONS

Birkinshaw, J. Chem Soc. Perkins Trans. I 147 (1984).

Primary Examiner—Robert Gerstl
Attorney, Agent, or Firm—Jacobson, Price, Holman & Stern

[57] ABSTRACT

The invention relates to the derivatives of formula I:

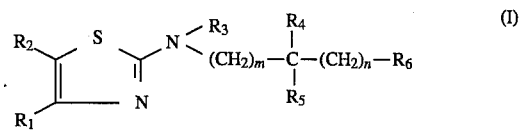

in which $R_1$ represents a phenyl or naphthyl radical (optionally substituted), $R_2$ represents a hydrogen or halogen atom or an alkyl, hydroxymethyl or formyl radical, $R_3$ represents an alkyl, cycloalkyl, alkenyl, cycloalkylalkyl or phenyl radical, $R_4$ represents a hydrogen atom or an alkyl, cycloalkyl or cycloalkylalkyl radical, $R_5$ represents an alkyl, cycloalkyl, cycloalkylalkyl or alkenyl radical or a radical of formula B:

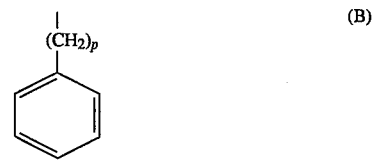

(p=0, 1, 2 or 3), $R_6$ represents a phenyl, pyridyl, imidazolyl, pyrrolyl, thienyl or furyl radical, optionally substituted, or a cycloalkyl radical, m and n, which may be identical or different, each represent 0 or 1, their possible stereoisomers and their addition salts.

10 Claims, No Drawings

BRANCHED ALKYLAMINO DERIVATIVES OF THIAZOLE, PROCESSES FOR PREPARING THEM AND PHARMACEUTICAL COMPOSITIONS CONTAINING THEM

The present invention relates to branched alkylamino derivatives of thiazole, to processes for preparing them and to pharmaceutical compositions containing them.

Several 2-aminothiazole derivatives are already known. Patent Application EP-0,462,264 described 2-aminothiazole derivatives in which the tertiary amine at position 2 contains two substituents each having at least one hetero atom. These substituents are derivatives of aromatic or aliphatic amines, or else derivatives of acids, of ketones, of amides or of thioketones. All these compounds are PAF-acether antagonists and find their applications in the treatment of asthma, certain allergic or inflammatory states, cardiovascular diseases, hypertension and various renal pathologies, or alternatively as contraceptive agents. Application GB-2,022,285 describes compounds possessing regulatory activity with respect to the immune response and having anti-inflammatory properties. They are thiazole derivatives substituted at position 2 with secondary amine groups.

Some heterocyclic derivatives of 2-(acylamino)thiazole have been described in Patent Application EP-0,432,040. These compounds are cholecystokinin and gastrin antagonists. 2-Amino-4,5-diphenylthiazole derivatives having anti-inflammatory properties are also known (Patent Application JP-01 75 475). 2-Amino-4-(4-hydroxyphenyl)thiazole derivatives which are useful as synthesis intermediates for the preparation of 2,2-diarylchromenothiazole derivatives are also known (Patent Application EP-0,205,069). 2-(N-Methyl-N-benzylamino)thiazole derivatives are also described in J. Chem. Soc. Perkin, Trans 1, (1984), 2, pp. 147–153 and in J. Chem. Soc. Perkin, Trans 1, (1983), 2, pp. 341–347.

Patent Application EP-0,283,390, describes and claims, among other thiazole derivatives, 2-[N-alkyl-N-(pyridylalkyl)amino]thiazole derivatives of formula:

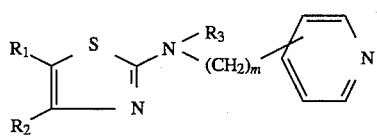

These derivatives, in which the amine at position 2 is substituted with a pyridyl(unbranched alkyl) radical, are endowed with advantageous pharmacological properties and possess, in particular, stimulant activity with respect to central cholinergic transmission. They may hence be used as muscarinic receptor agonists and find their applications in the treatment of memory disorders and senile dementia.

Compounds of the present invention differ from other 2-aminothiazole derivatives described in the literature in respect of their novel structures and their novel pharmacological properties.

They are 2-aminothiazole derivatives in which the amine at position 2 is a tertiary amine having an alkyl or aryl-(branched alkyl) substituent.

This particular structure endows the products of the invention with very advantageous pharmacological properties. In effect, the compounds of the invention displace at very low concentrations—less than 10 μM—the binding of $^{125}$I-CRF to specific receptors present on rat cortex membranes. The compounds of the invention are hence modulators of the effects of corticotropin-releasing factor (CRF), a neuropeptide which controls the activity of the hypothalamohypophysioadrenal axis, and find their applications in the treatment of stress-related ailments, and more generally in the treatment of pathologies involving CRF such as, for example, psychiatric disorders, anxiety, anorexia nervosa or the like.

The subject of the present invention is, more especially, the branched alkylamino derivatives of thiazole of formula I:

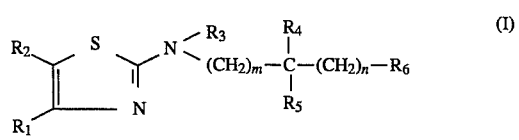

in which:

$R_1$ represents a radical of formula $A_1$ or a radical of formula $A_2$:

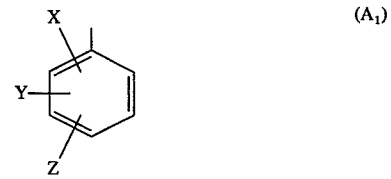

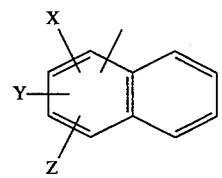

(in which formulae X, Y and Z, which may be identical or different, each represent a hydrogen atom, a halogen atom, an alkoxy radical containing 1 to 5 carbon atoms, an alkyl radical containing 1 to 5 carbon atoms, a hydroxyl radical, a cyano radical, a nitro radical, a trifluoromethyl radical or an aralkyl radical containing 7 to 9 carbon atoms), $R_2$ represents a hydrogen atom, a halogen atom, an alkyl radical containing 1 to 5 carbon atoms, a hydroxymethyl radical or a formyl radical, $R_3$ represents an alkyl radical containing 1 to 5 carbon atoms, a cycloalkyl radical containing 3 to 8 carbon atoms, an alkenyl radical containing 2 to 6 carbon atoms, a cycloalkylalkyl radical containing 4 to 8 carbon atoms or a phenyl radical, $R_4$ represents a hydrogen atom, an alkyl radical containing 1 to 5 carbon atoms, a cycloalkyl radical containing 3 to 6 carbon atoms or a cycloalkylalkyl radical containing 4 to 8 carbon atoms and having a linear or branched chain, $R_5$ represents an alkyl radical containing 1 to 5 carbon atoms, a cycloalkyl radical containing 3 to 8 carbon atoms and optionally substituted with alkyl radicals containing 1 to 5 carbon atoms, a cycloalkylalkyl radical containing 4 to 8 carbon atoms and having a linear or branched chain, an alkenyl radical containing 2 to 6 carbon atoms or a radical of the formula B:

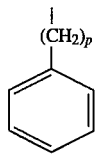

(B)

(in which formula p is equal to 0, 1, 2 or 3), $R_6$ represents a phenyl radical, a pyridyl radical, an imidazolyl radical, a pyrrolyl radical, a thienyl radical or a furyl radical (which radicals are optionally substituted with one or more halogen atoms, with alkoxy radicals containing 1 to 5 carbon atoms, with alkyl radicals containing 1 to 5 carbon atoms, with hydroxyl radicals, with cyano radicals, with nitro radicals, with trifluoromethyl radicals, with methylthio radicals or with radicals of formula B), or a cycloalkyl radical containing 3 to 8 carbon atoms and optionally substituted with alkyl radicals containing 1 to 5 carbon atoms, m and n, which may be identical or different each represent 0 or 1, their stereoisomers and their addition salts with an inorganic or organic acid.

Preferred compounds of the invention are the compounds of the formula I in which:

$R_1$ represents a radical of formula $A_1$, $R_2$ represents a halogen atom or an alkyl radical containing 1 to 5 carbon atoms, $R_3$ represents an alkyl radical containing 1 to 5 carbon atoms, a cycloalkyl radical containing 3 to 8 carbon atoms or an alkenyl radical containing 2 to 6 carbon atoms, $R_5$ represents an alkyl radical containing 1 to 5 carbon atoms, a cycloalkyl radical containing 3 to 8 carbon atoms and optionally substituted with alkyl radicals containing 1 to 5 carbon atoms or a cycloalkylalkyl radical containing 4 to 8 carbon atoms and having a linear or branched chain, and $R_4$, $R_6$, m and n have the same meaning as for the formula I, their stereoisomers and also their addition salts with an inorganic or organic acid.

Among these, an especially preferred group of compounds may be represented by the formula $I_A$:

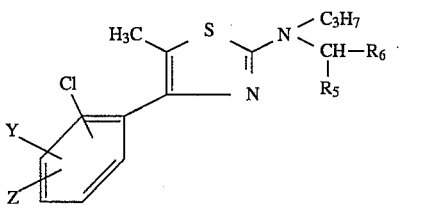

(I$_A$)

in which:

Y and Z have the same meaning as for the formula I, $R_5$ represents an alkyl radical containing 1 to 5 carbon atoms or a cycloalkyl radical containing 3 to 8 carbon atoms, and optionally substituted with alkyl radicals containing 1 to 5 carbon atoms or a cycloalkylalkyl radical containing 4 to 8 carbon atoms and having a linear or branched chain, $R_6$ represents a phenyl radical or a pyridyl radical (which radicals are optionally substituted with one or more halogen atoms, alkoxy radicals containing 1 to 5 carbon atoms, with alkyl radicals containing 1 to 5 carbon atoms, hydroxyl radicals, cyano radicals, nitro radicals, trifluoromethyl radicals or with methylthio radicals), an imidazolyl radical optionally substituted with an alkyl radical containing 1 to 5 carbon atoms, or a cycloalkyl radical containing 3 to 8 carbon atoms and optionally substituted with alkyl radicals containing 1 to 5 carbon atoms, their stereoisomers and their addition salts with an inorganic or organic acid.

The —$C_3H_7$ radical of the formula $I_A$ represents an n-propyl radical.

The term alkyl radical or alkenyl radical is understood to mean linear or branched radicals.

The following compounds may be mentioned among the preferred compounds of the invention:

4-(4-chloro-2-methoxyphenyl)-5-methyl-2-{N-propyl-N-[1-(4-pyridyl)ethyl]amino}thiazole, 4-(4-chloro-2-methylphenyl)-5-methyl-2{N-propyl-N-[1-(4-pyridyl)ethyl]amino}thiazole, 4-(2-chloro-4-methylphenyl)-5-methyl-2-{N-propyl-N-[1-(4-pyridyl)ethyl]amino}thiazole, 4-(2-chloro-4-methoxyphenyl)-5-methyl-2-{N-propyl-N-[1-(4-pyridyl)ethyl]amino}thiazole, 5-bromo-4-(2,4-dichlorophenyl)-2-{N-propyl-N-[1-(4-pyridyl)ethyl]amino}thiazole, 4-(2,4-dichlorophenyl)-5-methyl-2-{N-(2-propenyl)-N-[1-(4-pyridyl)ethyl]amino}thiazole, 4-(2,4-dichlorophenyl)-5-methyl-2-[N-(α-methylbenzyl)-N-propylamino]thiazole, 4-(2,4-dichlorophenyl)-5-methyl-2-{N-[cyclopropyl(4-pyridyl)methyl]-N-propylamino}thiazole, 4-(2,4-dichlorophenyl)-5-methyl-2-{N-propyl-N-[1-(4-pyridyl)ethyl]amino}thiazole, 4-(2,4-dichlorophenyl)-5-methyl-2-{N-[1-(2-methyl-4-pyridyl)ethyl]-N-propylamino} thiazole, 4-(2,4-dichlorophenyl)-5-methyl-2-{N-[1-(4imidazolyl)ethyl]-N-propylamino}thiazole, 4-(2,4-dichlorophenyl)-5-methyl-2-{N-propyl-N-[1-(4-pyridyl)propyl]amino}thiazole, 4-(2,4-dichlorophenyl)-5-methyl-2-{N-[2-methyl-1-(4-pyridyl)propyl]-N-propylamino}thiazole, 4-(2,4-dichlorophenyl)-5-methyl-2-[N-(α-cyclopropylbenzyl)-N-propylamino]thiazole, 4-(2,4-dichlorophenyl)-5-methyl-2-[N-(α-cyclopropyl-4-methoxybenzyl)-N-propylamino]thiazole, 4-(2,4-dichlorophenyl)-5-methyl-2-{N-[cyclopropyl(2-thienyl)methyl]-N-propylamino}thiazole, 4-(2,4-dichlorophenyl)-5-methyl-2-[N-(dicyclopropylmethyl)-N-propylamino]thiazole, 4-(2,4-dichlorophenyl)-5-methyl-2-[N-(α-cyclopentylbenzyl)-N-propylamino]thiazole, 4-(2,4-dichlorophenyl)-5-methyl-2-{N-[cyclopentyl(4-pyridyl)methyl]-N-propylamino}thiazole, 4-(2,4-dichlorophenyl)-5-methyl-2-[N-(α-cyclopropyl-4-fluorobenzyl)-N-propylamino]thiazole, 4-(2,4-dichlorophenyl)-5-methyl-2-{N-[(3-chloro-4-pyridyl)(cyclopropyl)methyl]-N-propylamino} thiazole, 4-(2,4-dichlorophenyl)-5-methyl-2-{N-propyl-N-[α-(4-pyridyl)benzyl]amino}thiazole, 4-(2,4-dichlorophenyl)-5-methyl-2-{N-[cyclopropyl(4-imidazolyl)methyl]-N-propylamino}thiazole, 4-(2,4-dichlorophenyl)-5-methyl-2-{N-[α-cyclopropyl-3(trifluoromethyl)benzyl]-N-propylamino} thiazole, 4-(2,4-dichlorophenyl)-5-methyl-2-{N-[cyclopentyl(cyclopropyl)methyl]-N-propylamino}thiazole, 4-(2,4-dichlorophenyl)-5-methyl-2-{N-[cyclopropyl(1-methyl-4-imidazolyl)methyl]-N-propylamino}thiazole, 4-(2,4-dichlorophenyl)-5-methyl-2-{N-[cyclopropyl(1-benzyl-4-imidazolyl)methyl]-N-propylamino}thiazole, 4-(2,4-dichlorophenyl)-5-methyl-2-{N-[cyclopropyl(2-pyridyl)methyl]-N-propylamino}thiazole, 4-(2-chloro-4-methylphenyl)-5-methyl-2-[N-(dicyclopropylmethyl)-N-propylamino]thiazole, 4-(2,4-dichlorophenyl)-5-methyl-2-{N-[cyclopropyl(3-pyridyl)methyl]-N-propylamino}thiazole, 4-(2-chloro-4-methoxyphenyl)-5-methyl-2-[N-(dicyclopropylmethyl)-N-propylamino]thiazole, 4-(2,4-dichlorophenyl)-5-methyl-2-[N-(α-cyclobutylbenzyl)-N-propylamino]thiazole, 4-(2,4-dichlorophenyl)-5-methyl-2-[N-(2,2-dicyclopropylethyl)-N-propylamino]thiazole.

All these compounds can be either in free base form or in salified form.

The subject of the present invention is also a process for preparing the compounds of formula I, characterised in that an alpha-halo, and preferably an alpha-bromo, carbonyl derivative of formula II:

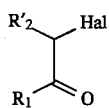   (II)

in which
R₁ has the same meaning as for the formula I, R'₂ represents a hydrogen atom or an alkyl radical containing 1 to 5 carbon atoms and Hal represents a halogen atom, is reacted either with a thiourea of formula III:

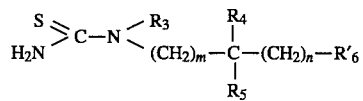   (III)

in which R₃, R₄, R₅, m and n have the same meaning as for the formula I, and R'₆ has the same meaning as R₆ except in the case where R₆ contains functions with reactive nitrogen atoms, where R'₆ then denotes the radical corresponding to R₆ in which a hydrogen of the said reactive function has been replaced by a protective group that withstands hydrolysis in an alkaline medium, to form a compound of formula I':

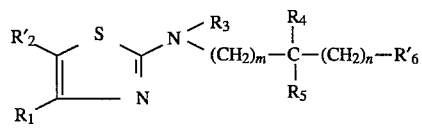   (I')

in which
R₁, R₃, R₄, R₅, m and n have the same meaning as for the formula I,

R'₂ has the meaning given for the formula II, and

R'₆ has the meaning given for the formula III, or with a thiourea of formula III_A:

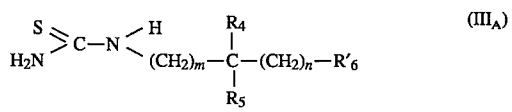   (III_A)

in which R₄, R₅, m and n have the same meaning as for the formula I, and R'₆ has the meaning given for the formula III, to form the compounds of formula IV:

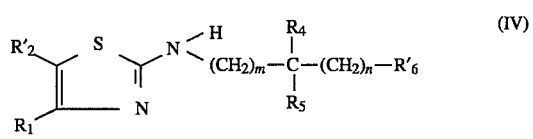   (IV)

in which R₁, R₄, R₅, m and n have the same meaning as for formula I, R'₂ has the meaning given for the formula II and R'₆ has the meaning given for the formula III, which is reacted with a halide of formula V:

Hal—R₃   (V)

in which Hal represents a halogen atom and R₃ has the same meaning as for the formula I, to form the compound of formula I', and then, the compounds of formula I' in which R'₂ represents a hydrogen atom are subjected
either to the action of a halogen, to form the compounds of the formula I in which R₂ represents a halogen atom, which can then, when R₂ represents a bromine atom, be subjected to the action of another halogen to form the compounds of formula I in which R₂ represents this halogen atom,
or to the action of oxalyl chloride, to prepare the compounds of the formula I in which R₂ represents a formyl radical, which can then be subjected to a reduction to obtain the compounds of formula I in which R₆ represents a hydroxymethyl radical, or the compounds of formula I' in which R'₆ represents a radical R₆ containing functions with reactive nitrogen atoms having a protective group are subjected to an acid hydrolysis, to obtain the compounds of formula I in which R₆ represents a radical containing a primary or secondary amine, and, where appropriate, the compounds of formula I are then separated into their possible stereoisomers and/or salified with an organic or inorganic acid to form the corresponding salts.

The compounds of formula IV, which are useful intermediates for the preparation of the compounds of formula I, also form part of the invention.

The derivatives of formula II may be obtained from the corresponding unhalogenated ketones of formula R₁—CO—CH₂—R'₂, either by the action of bromine in a suitable organic solvent such as acetic acid, carbon tetrachloride or ethyl ether, or by the action of quaternary ammonium tribromides according to the method described in Bull. Chem. Soc. Japan (1987), 60, pp. 1159–1160 and pp. 2667–2668, or else by the action of cupric bromide in an organic solvent such as a mixture of chloroform and ethyl acetate (J. Org. Chem. (1964), 29, pp. 3451–3461).

The ketones of formula R₁—CO—CH₂—R'₂ are, in general, known and commercially available products. These compounds may be prepared by the Friedel-Crafts reaction between a compound of formula R₁H and an acyl halide of formula R'₂COHal, preferably an acyl chloride of formula R'₂CH₂COCl, in the presence of a Lewis acid.

The compounds of formula II in which R₁ represents a radical of formula A₁ substituted at positions 2 and 4 with a halogen atom, and R'₂ represents a methyl radical, may be obtained from halogenated benzene derivatives, and in particular using 1,3-dihalogenated benzenes, which are reacted with 2-bromopropionyl bromide in the presence of aluminium chloride.

The compounds of formula II and III$_A$ are obtained from the compounds of formula VI:

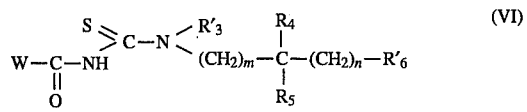

in which R'₃ has the same meaning as the formula I or represents a hydrogen atom, R'₆ has the meaning given for the formula III and W represents a phenyl radical or a tert-butyl radical, either by an acid treatment preferably using hydrochloric acid, or by a basic treatment preferably using sodium hydroxide.

When W is a phenyl radical, treatment with an inorganic acid is particularly used when R'₆ represents a pyridyl radical. A basic treatment is performed when R₅ is a cycloalkyl group, for example a cyclopropyl, and when R₆ is an imidazolyl radical substituted on the nitrogen with a protective group that withstands hydrolysis in an alkaline medium.

When W represents a tert-butyl radical, the thiourea derivatives of formulae III and III$_A$ are obtained from the compounds of formula VI by the action of a strong acid, for example concentrated hydrochloric acid, at a temperature of between 10° C. and 100° C.

The compounds of formula VI are obtained by reacting benzoyl isothiocyanate or pivaloyl isothiocyanate with the amines of formula VII:

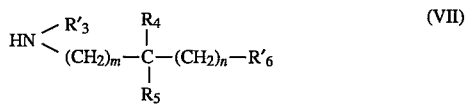

in which,

R₄, R₅, m and n have the same meaning as for the formula I, R'₃ has the meaning given for the formula VI and R'₆ has the meaning given for the formula III.

The amines of formula VII, where secondary amines are concerned, may be prepared by standard methods.

According to a first method, alkylation of the corresponding primary amine VII$_A$:

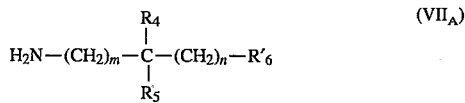

is performed with an alkyl halide Hal—R₃ of formula V, preferably in the heated state, in the presence of an alkali metal salt in a polar organic solvent, for example dimethylformamide.

According to another method of alkylation, the amines of formula VII$_A$ are subjected to the action of an acid halide or acid anhydride in an organic solvent chosen from halogenated hydrocarbons such as methylene chloride, in the presence of a proton acceptor, preferably triethylamine. The amide derived from this reaction is then reduced with hydrides (AlLiH₄ or the like) in organic solvents of the ether type.

The two methods mentioned above are used preferentially for the preparation of the compounds of formula VII in the form of pure isomers.

Another method of preparation of the compounds of the formula VII consists in condensing a primary amine of formula R₃NH₂ with a ketone in a dehydrating medium, to form the corresponding imine, which is then reduced in a conventional manner with a metal hydride, preferably sodium borohydride, or with hydrogen in the presence of a suitable catalyst. In the reaction of the primary amine of formula R₃NH₂ with a ketone in a dehydrating medium, it is preferable to use either titanium IV chloride (TiCl₄) or a catalysis with para-toluenesulphonic acid.

The amines of formula VII in which m and n are equal to zero are preferably prepared according to a method the principle of which is given in the following scheme: Step A

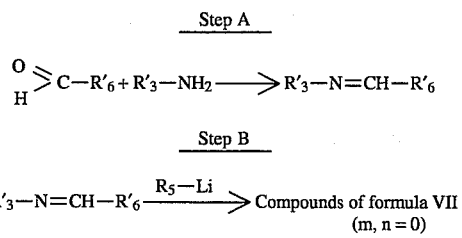

The condensation of the aldehyde with the primary amine in Step A preferably carried out in ethanol or in toluene at room temperature, and the reaction of the imine with an alkyllithium derivative in Step B is carried out in ethyl ether or tetrahydrofuran at a temperature of 0° C. and 15° C.

As already mentioned above, when the substituent R₆ possesses reactive functions, these functions must be protected in a conventional manner. For example, when R₆ represents an imidazolyl radical, its reactive (NH) group may be blocked with a trityl group. After formation of the derivatives of formula I, removal of the protective group is carried out using an inorganic acid, for example hydrochloric acid. If so desired, it is then possible to prepare derivatives substituted on the imidazole radical. To this end, the compounds of formula I in which R₆ represents an imidazolyl group are reacted with, for example, an alkyl halide or an aralkyl halide. The reaction is performed in the presence of an alkali metal salt in a polar organic solvent, for example dimethylformamide, preferably in the heated state. N-alkyl- or N-aralkylimidazolyl derivatives are thereby obtained.

The alkylation of the compounds of formula IV is performed in the presence of a base (sodium hydride, caesium carbonate, potassium carbonate, and the like). When the reaction is performed in the presence of alkali metal carbonates, polar solvents, for example dimethylformamide, are used as a solvent. When the alkylation is performed in the presence of hydrides, tetrahydrofuran is preferably used. It is also possible to use aromatic hydrocarbons. When the reaction is performed in the presence of lithium amide, tetrahydrofuran is preferably used as a solvent. The reaction of the compounds of formula II with the thioureas of formula III or IIIa is performed in an organic medium in the presence of an organic base, for example triethylamine.

For the preparation of the thiazole derivatives of formula I substituted at position 5 with a halogen atom, from the compounds of formula I unsubstituted at position 5, the reaction is performed at room temperature using an alkyl halide as a solvent and preferably in the presence of a proton acceptor.

The compounds of formula I substituted at position 5 with a halogen atom may be prepared from their analogues, compounds of formula I substituted at position 5 with a bromine atom. The latter compounds are subjected to the action of a halogenating agent after a halogen/metal exchange.

The thiazole derivatives of formula I substituted at position 5 with a formyl radical are obtained from the corresponding derivatives unsubstituted at position 5 after reaction with oxalyl chloride. The reaction is preferably performed in an organic solvent such as dimethylformamide. On subjecting the thiazole derivatives of formula I substituted at position 5 with a formyl radical to the action of a reducing agent such as sodium borohydride, the compounds of formula I substituted at position 5 of the thiazole heterocycle with a hydroxymethyl radical are obtained. The reaction is performed in an alcoholic solvent at a temperature of approximately 0° C.–35° C.

The compounds of formula I in which $R_1$ represents a radical of formula $A_1$ or $A_2$ substituted with at least one hydroxyl radical are obtained from the compounds of formula I in which $R_1$ represents a radical of formula $A_1$ or of formula $A_2$ substituted with one or more methoxy radicals. To this end, the latter products are subjected to the action of an acid, for example hydrobromic acid. In this case, the reaction is performed in the heated state.

The salts of the compounds of formula I with pharmaceutically acceptable acids or bases are the preferred salts, but those which make it possible to isolate the compounds of formula I, in particular to purify them or to obtain pure isomers, are also subjects of the invention.

Among pharmaceutically acceptable acids for the preparation of addition salts with the compounds of formula I, there may be mentioned hydrochloric, phosphoric, fumaric, citric, oxalic, sulphuric, ascorbic, tartaric, maleic, mandelic, methanesulphonic, lactobionic, gluconic, glucaric, hydroxyethylmethanesulphonic, succinylsulphonic, and the like, acids.

The compounds of the present invention possess highly advantageous pharmacological properties. The compounds of the invention displace, in particular at concentrations of less than 10 μM (0.01–10 μM), the binding of $^{125}$I-CRF to specific receptors present on rat cortex membranes, according to the method described by De Souza E. B. (J. Neurosci (1987), 7 (1), pp. 88–100). This is surprising and unexpected, since compounds of structure close to that of the compounds of the invention, but in which the amine at position 2 of the thiazole ring does not contain a branched substituent, do not significantly displace $^{125}$I-CRF binding.

In effect, the 2-[N-methyl-N-(3-pyridylmethyl)amino]-4-(2,4,6-trimethylphenyl)thiazole, a compound described in Example 112 of Patent Application EP-0,283,390, produces a displacement of only approximately 8% at a concentration of $10^{-5}$M.

Corticotropin-releasing factor (CRF) is a neuropeptide which controls the activity of the hypothalamohypophysioadrenal axis. This factor is responsible for stress-related endocrine and behavioural responses.

In effect, it has been demonstrated that CRF can modulate behaviour, as well as certain functions of the autonomous nervous system (G. F. Koob, F. E. Bloom, Fed. Proc. (1985), 44, p. 259; M. R. Brown, L. A. Fisher, Fed. Proc. (1985), 44, p. 243). More especially, CRF induces the secretion of corticotropin (ACTH), β-endorphin and other peptides derived from pro-opiomelanocortin (A. Tazi et al., Regul. Peptides (1987) 18, p. 37; M. R. Brown et al., Regul. Peptides (1986) 16, p. 321; C. L. Williams et al., Am. J. Physiol. (1987), G 582, p. 253).

The compounds of the invention may hence be useful for regulation of the secretion of these endogenous substances. They find their applications more especially for decreasing the response to stress (behaviour, emotional states, gastrointestinal and cardiovascular disorders, disorders of the immune system), and more generally in pathologies involving CRF, for example psychiatric disorders, anxiety, anorexia nervosa or the like.

The invention also extends to pharmaceutical compositions containing as active principle at least one compound of general formula I, or one of its salts with a pharmaceutically compatible inorganic or organic acid, in combination with one or more inert and suitable excipients.

The pharmaceutical compositions thereby obtained are advantageously presented in various forms such as, for example, tablets, dragées, hard gelatin capsules, suppositories, and solutions for injection or for oral use.

The dosage can vary widely in accordance with the patient's age and weight, the nature and severity of the ailment and also the administration route. Generally speaking, single doses will range between 0.5 mg and 200 mg, and the daily dosage which can be used in human therapy, between 0.5 mg and 800 mg.

The preferred administration route is the oral or parenteral route.

The examples which follow, given without implied limitation, illustrate the invention.

The melting points were measured according to the Micro-Kofler technique.

The proton nuclear magnetic resonance ($^1$H NMR) spectra of the compounds of formula I were recorded, as appropriate, at 200 MHz to 100 MHz or at 80 MHz.

The compounds of the invention possess a percentage analysis which is in agreement with the theoretical value.

PREPARATIONS

PREPARATION OF THE COMPOUNDS OF THE FORMULA II

PREPARATION I 2-bromo-1-(2,4,6-trimethylphenyl)-1-ethanone (Compound 1)

Dissolve 0.3 mol of 1-(2,4,6-trimethylphenyl)-1-ethanone in 200 ml of glacial acetic acid, and add 31.8 g of bromine dropwise while maintaining the reaction medium at a temperature below 10° C. When the addition is complete, allow the reaction medium to return to room temperature and leave at this temperature for 2 hours. Then pour the reaction medium into 500 ml of ice-cold water and extract the aqueous phase with ethyl ether. Wash the organic extracts with saturated aqueous sodium bicarbonate solution and then with salt water, and dry over anhydrous magnesium sulphate.

After evaporation of the solvent, an oil is obtained, which may be used without further purification.

Other compounds (Compounds 2 to 13)

The following compounds were obtained according to the method described for the preparation of 2-bromo-1-(2,4,6-trimethylphenyl)-1-ethanone, using the appropriate ketones as starting materials.

Compound 2: 2-bromo-1-(2-naphthyl)-1-propanone
Compound 3: 2-bromo-1-(2,4-dimethylphenyl)-1-propanone
Compound 4: 2-bromo-1-(4-chloro-2-methylphenyl)-1-propanone
Compound 5: 2-bromo-1-(2-chloro-4-methylphenyl)-1-propanone
Compound 6: 2-bromo-1-(2-chloro-4-methoxyphenyl)-1-propanone
Compound 7: 2-bromo-1-(2,4-dimethoxyphenyl)-1-propanone
Compound 8: 2-bromo-1-(4-chlorophenyl)-1-propanone
Compound 9: 2-bromo-1-(1-naphthyl)-1-propanone
Compound 10: 2-bromo-1-(2,4-dichlorophenyl)-1-ethanone
Compound 11: 2-bromo-1-(4-methoxyphenyl)-1-propanone
Compound 12: 2-bromo-1-(4-chloro-2-methoxyphenyl)-1-propanone
Compound 13: 2-bromo-1-(4-methylphenyl)-1-propanone

PREPARATION II 2-bromo-1-(2,4,6-trimethoxyphenyl)-1-propanone (Compound 14)

Bring a suspension of 45.3 g of cupric bromide in 150 ml of ethyl acetate to reflux, and add 25.1 g of 1-(2,4,6-trimethoxyphenyl)-1-propanone, dissolved in 150 ml of chloroform, rapidly at this temperature. A copious greenish-yellow precipitate appears.

Bring the reaction medium to reflux for 2 hours 30 minutes. Then allow it to return to room temperature, filter off the insoluble salts and wash with ethyl acetate.

The organic phases are treated with animal charcoal. After removal of the solid by filtration, concentrate under reduced pressure to obtain an oil. Purify by chromatography on a silica column, using a mixture of cyclohexane and ethyl acetate (6:4 V/V) as eluent.

Oil. Yield: 60%

PREPARATION III 2-bromo-1-(2,4-dichlorophenyl)-1-propanone (Compound 15)

Add 17.4 g of tert-butylammonium tribromide at room temperature to 7 g of 1-(2,4-dichlorophenyl)-1-propanone dissolved in a mixture of 420 ml of methylene chloride and 140 ml of methanol.

After 24 hours, evaporate the reaction medium to dryness under vacuum.

Take up with water, extract with ethyl acetate, dry the organic phase with sodium sulphate.

Evaporate under vacuum, then purify on a silica column, using a mixture of cyclohexane and ethyl acetate (20:1 V/V) as eluent.

Oil. Yield: 78%

2-Bromo-1-(2-chloro-4-methoxyphenyl)-1-propanone (Compound 6) may also be obtained in the same manner.

PREPARATION IV 2-bromo-1-(2,4-dibromophenyl)-1-propanone (Compound 16)

Add 15 g of aluminium chloride cautiously at 0° C. to 25 g of 1,3-dibromobenzene in 250 ml of carbon disulphide, and then run in 22.86 g of 2-bromopropionyl bromide slowly.

Bring to reflux for 8 hours, then evaporate off the carbon disulphide under vacuum and pour the reaction medium onto crushed ice.

Extract twice with heptane, dry, evaporate to dryness and then purify on a silica column, using a mixture of cyclohexane and ethyl acetate (10:1 V/V) as eluent, to obtain the expected product.

Yield: 76%.

The process described above may be used to prepare 2-bromo-1-(2,4-dichlorophenyl)-1-propanone (Compound 15), as well as 2-bromo-1-(3,5-dichlorophenyl)-1-propanone (Compound 17).

In the same manner, 2-bromo-1-(2-chloro-4-iodophenyl)-1-propanone (Compound 18) was prepared using 1-chloro-3-iodobenzene instead of 1,3-dibromobenzene as starting material.

PREPARATION OF THE COMPOUNDS OF FORMULA VII

PREPARATION V

N-(α-cyclopropylbenzyl)propylamine (Compound 19)

To 10 g of cyclopropyl phenyl ketone in 60 ml of anhydrous toluene, add 4 Å molecular sieve and 100 mg of para-toluenesulphonic acid, then 6 g of propylamine.

Imine formation is monitored by gas chromatographic assay. After six days of heating at 55° C., cool the reaction mixture, filter off the molecular sieve and evaporate to dryness under vacuum.

Take up the residue in 100 ml of anhydrous ethanol. Cool to 0° C. and add 2.65 g of sodium borohydride in small portions. After overnight stirring at room temperature, evaporate to dryness under vacuum, take up in water, hydrolyse with N hydrochloric acid to take the pH to 2 and wash with ethyl acetate. Take to pH 9 by adding 2N sodium hydroxide and then extract several times with methylene chloride.

The organic phase, after drying and evaporation, gives an oil which may be used directly.

Yield: 60%

Proton nuclear magnetic resonance spectrum (solvent $CDCl_3$): 0.15–1.7 ppm, m, 11H; 2.4 ppm, t+d, 2H; 2.80 ppm, d, 1H; 7.3–7.4 ppm, m, 5H.

Other compounds (Compounds 20 to 47)

The amines shown in Table 1 are obtained according to the process described above.

TABLE I
HN−R₃
  |
  CH−R₆
  |
  R₅
| Compound | R₃ | R₅ | R₆ |
|---|---|---|---|
| 20 | −C₃H₇ |  | 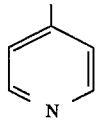 |
| 21 | −C₃H₇ |  | 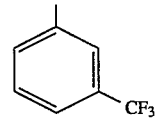 |
| 22 | −C₃H₇ | −CH₃ | 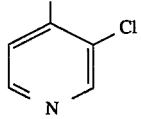 |
| 23 | −C₃H₇ | −CH₃ | 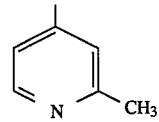 |
| 24 | −C₃H₇ | −CH₃ | 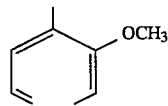 |
| 25 | −C₃H₇ | −C₂H₅ |  |
| 26 | −C₃H₇ |  |  |
| 27 | −C₃H₇ |  | 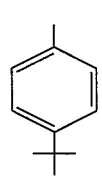 |
| 28 | −C₃H₇ |  | 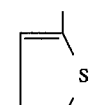 |
| 29 | −C₃H₇ | 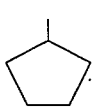 | 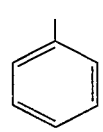 |

TABLE I-continued

HN–CH(R3)(R5)–R6 structure with R3 on HN, and CH bearing R5 and R6

| Compound | R3 | R5 | R6 |
|---|---|---|---|
| 30 | —C3H7 | cyclopentyl | 4-pyridyl |
| 31 | —C3H7 | cyclopropyl | 4-fluorophenyl |
| 32 | —C3H7 | cyclopropyl | 3-chloro-4-pyridyl |
| 33 | —C3H7 | —CH3 | 1-trityl-imidazol-4-yl |
| 34 | —C3H7 | cyclopropyl | cyclopropyl |
| 35 | —C3H7 | —CH3 | 4-pyridyl |
| 36 | —C3H7 | —CH3 | 3-pyridyl |
| 37 | —CH2CH(CH3)CH3 | —CH3 | 4-pyridyl |
| 38 | —CH3 | —CH3 | 2,3-dimethyl-4-pyridyl |

TABLE I-continued $$HN\begin{matrix}R_3\\\diagdown\\CH-R_6\\|\\R_5\end{matrix}$$

| Compound | $R_3$ | $R_5$ | $R_6$ |
|---|---|---|---|
| 39 | $-C_2H_5$ | $-CH_3$ | 4-pyridyl |
| 40 | cyclopropyl | $-CH_3$ | 3-pyridyl |
| 41 | $-C_3H_7$ | cyclobutyl | phenyl |
| 42 | $-C_3H_7$ | cyclopropyl | 4-bromophenyl |
| 43 | $-C_3H_7$ | cyclopropyl | 4-chlorophenyl |
| 44 | $-C_3H_7$ | $-CH_3$ | cyclopropyl |
| 45 | $-C_3H_7$ | cyclopropyl | cyclobutyl |
| 46 | $-C_3H_7$ | $-CH_2-$phenyl | cyclopropyl |
| 47 | $-C_3H_7$ | $-CH_3$ | 2-chloro-4-pyridyl |

PREPARATION VI

N-[cyclopropyl(4-pyridyl)methyl]propylamine (Compound 20)

N-[Cyclopropyl(4-pyridyl)methyl]propylamine may also be prepared in the following manner:

Step A

Dissolve 1.07 g of 4-pyridinecarbaldehyde in 10 ml of absolute ethanol and add 0.8 g of n-propylamine slowly.

After 30 minutes of stirring, evaporate to dryness to obtain 1.48 g of oil.

Yield: 99%

Step B

Dissolve the imine obtained in the preceding step in 10 ml of anhydrous isopropyl ether.

Add this solution with stirring at 0° C. to 30 ml of a solution of cyclopropyllithium (20 mmol) in isopropyl ether. After two hours of stirring at room temperature, cool to 0° C. and add dropwise 3 ml of methanol, then 10 ml of 30% aqueous ammonium chloride solution.

Extract the ether phase with N hydrochloric acid.

Neutralise the acidic aqueous phase with sodium bicarbonate and then extract with ethyl acetate.

Dry over anhydrous sodium sulphate and evaporate to dryness to obtain a colourless oil.

Yield: 80%

Proton nuclear magnetic resonance spectrum (solvent CDCl$_3$): 0.28–1.76 ppm, m, 8H; 0.88 ppm, t, 3H; 1.48 ppm, m, 2H; 2.31–2.49 ppm, m, 2H; 2.78 ppm, d, 1H; 7.35 ppm, dd, 2H; 8.54 ppm, dd, 2H.

Other compounds (Compounds 48 to 60)

The amines shown in Table II are obtained according to the process described above.

TABLE II

| Compound | R$_3$ | R$_5$ | R$_6$ |
|---|---|---|---|
| 48 | —C$_3$H$_7$ | 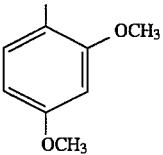 | 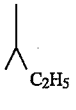 |
| 49 | —C$_3$H$_7$ | 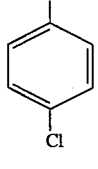 |  |
| 50 | —C$_3$H$_7$ | 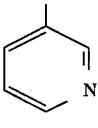 |  |
| 51 | —C$_3$H$_7$ | 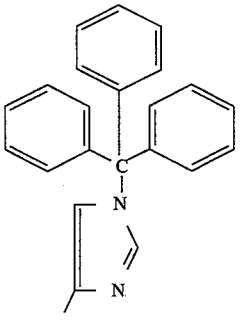 | 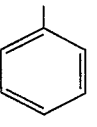 |
| 52 | —C$_3$H$_7$ | 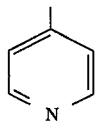 |  |

TABLE II-continued

| Compound | R$_3$ | R$_5$ | R$_6$ |
|---|---|---|---|
| 53 | —C$_3$H$_7$ |  | 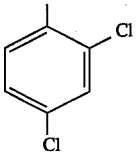 |
| 54 | —C$_3$H$_7$ |  | 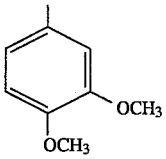 |
| 55 | —C$_3$H$_7$ |  | 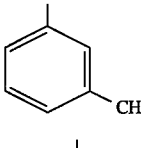 |
| 56 | —C$_3$H$_7$ |  |  |
| 57 |  |  | 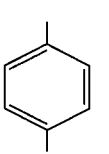 |
| 58 | —C$_3$H$_7$ |  | 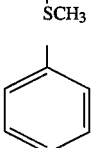 |
| 59 | —C$_3$H$_7$ |  | 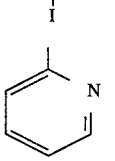 |
| 60 | —C$_3$H$_7$ |  |  |

PREPARATION VII

N-(cyclopropylmethyl)-1-(4-pyridyl)ethylamine (Compound 61)

Step A

Dissolve 3.2 ml of cyclopropane carboxylic acid in 20 ml of anhydrous methylene chloride under argon in a 250-ml three-necked flask. Cool in an ice bath and add 8.4 g of dicyclohexylcarbodiimide dissolved in 20 ml of anhydrous

21 methylene chloride. Stir for 30 minutes and add 5 g of 1-(4-pyridyl)ethylamine. After overnight stirring at room temperature, filter off and discard the white crystals. Evaporate the filtrate and purify the residue obtained on a silica column, using a mixture of ethyl acetate and hexane (1:9 V/V) as eluent, to obtain a white powder.

Yield: 95%

Step B

Dissolve 6 g of amide obtained in Step A in 20 ml of anhydrous tetrahydrofuran in a 250-ml three-necked flask equipped with a dropping funnel and a condenser. Heat to reflux and add 63 ml of a borane-dimethyl sulphide complex in solution (2N) in tetrahydrofuran. Heat to reflux for 3 hours. Cool and add 20 ml of 3N hydrochloric acid solution dropwise. Heat to reflux for one hour. Alkalinise with caustic soda and extract with ethyl acetate. Dry over anhydrous sodium sulphate and evaporate to dryness.

Yield: 88%

Proton nuclear magnetic resonance spectrum (solvent $CDCl_3$): 0.02–0.07 ppm, m, 2H; 0.37–0.50 ppm, m, 2H; 0.87–0.94 ppm, m, 1H; 1.33 ppm, d, 3H; 2.29 ppm, dd, 2H; 3.77 ppm, q, 1H; 7.22–7.25 ppm, dd, 2H; 8.53 ppm, d, 2H.

PREPARATION VIII

N-propyl-α-methylbenzylamine (Compound 62)

Introduce 23 ml of propylamine into 200 ml of dimethylformamide, add 32 g of caesium carbonate and 9.25 g of α-methylbenzyl bromide. Leave for 4 hours at room temperature. Evaporate to dryness and take up with water. Extract with ethyl acetate, dry over anhydrous sodium sulphate and evaporate to dryness to obtain the expected product.

Yield: 95%

Proton nuclear magnetic resonance spectrum (solvent $CDCl_3$): 0.86 ppm, t, 3H; 1.34 ppm, d, 3H; 1.17–1.64 ppm, m, 2H; 2.19–2.54 ppm, m, 2H; 3.75 ppm, q, 1H; 7.19–7.29 ppm, m, 5H.

PREPARATION IX

N-[cyclopropyl(3-pyridyl)methyl]propylamine (Compound 63)

Step A

Add 45 ml of a 0.625M solution of cyclopropyllithium in anhydrous ethyl ether dropwise and with stirring at −78° C. to 3 g of 3-pyridinecarbaldehyde in 70 ml of anhydrous ethyl ether. Allow to return to room temperature. Add water saturated with ammonium chloride, and extract with ethyl ether and then with methylene chloride.

Yield: 78%

Step B

Dissolve 3.35 g of cyclopropyl(3-pyridyl)methanol, the compound obtained in the preceding step, in 75 ml of dioxane and add 13.66 g of manganese dioxide. After 4 hours of stirring under reflux, filter the reaction medium while hot through Célite. The organic solution yields, after evaporating under vacuum, a residue which is purified by chromatography on a silica column, using a mixture of cyclohexane and ethyl acetate (1:1 V/V) as eluent, to obtain cyclopropyl 3-pyridyl ketone.

Yield: 80%

Proton nuclear magnetic resonance spectrum (solvent $CDCl_3$): 1.06–1.34 ppm, m, 4H; 2.68, m, 1H; 7.42 ppm, m, 1H; 8.23 ppm, m, 1H; 8.78 ppm, m, 1H; 9.26 ppm, m, 1H.

Step C

Proceed as described in Preparation V, using the ketone obtained in the preceding step, to obtain N-[cyclopropyl(3-pyridyl)methyl]propylamine.

22

PREPARATION X

N-[cyclopropyl(2-methyl-4-pyridyl)methyl]propylamine (Compound 64)

Step A

Add 130 ml of a 0.7M solution of cyclopropyllithium in tetrahydrofuran at −65° C. to 7.3 g of 4-cyano-2-methylpyridine in 100 ml of anhydrous tetrahydrofuran. After 4 hours of stirring, add methanol and ammonium sulphate solution (6.3 g in 20 ml of water). After extraction with ethyl ether, wash the organic phase with water, dry and evaporate under vacuum. The residue is purified on a silica column, using a mixture of methylene chloride and methanol (98:2 V/V) as eluent.

Cyclopropyl 2-methyl-4-pyridyl ketone is thereby obtained.

Yield: 59%

Proton nuclear magnetic resonance spectrum (solvent $CDCl_3$): 0.94–1.38 ppm, m, 4H;, 2.62 ppm, s, 3H; 2.52–2.65 ppm, m, 1H; 7.57 ppm, m, 2H; 8.65 ppm, d, 1H.

Step B

Proceed according to the method described in Preparation V, using the ketone obtained in the preceding step, to obtain N-[cyclopropyl(2-methyl-4-pyridyl)methyl]propylamine.

PREPARATION XI

N-(1,2-dicyclopropylethyl)propylamine (Compound 65)

Add 6.9 ml of propylamine to 2.2 g of cyclopropylmethyl cyclopropyl ketone in 85 ml of methylene chloride. Add 7 ml of a 1M solution of titanium (IV) chloride in methylene chloride dropwise at room temperature. After 18 hours stirring, add 40 ml of anhydrous methanol. Cool to 0° C. and add 1.0 g of sodium borohydride in small amounts. After overnight stirring at room temperature, add 10 ml of water and evaporate under vacuum. Take up in water and extract with methylene chloride. Extract with 2N hydrochloric acid. Wash with ethyl ether. Neutralise the aqueous phase with concentrated sodium hydroxide solution. Extract with methylene chloride, dry over anhydrous sodium sulphate and evaporate to dryness to obtain a colourless oil.

Yield: 76%

Proton nuclear magnetic resonance spectrum (solvent $CDCl_3$): 0.0–0.9 ppm, m, 13H; 1.2–1.75 ppm, m, 5H; 2.3–2.7 ppm, m, 2H.

Other compounds (Compounds 66 to 70)

The amines shown in Table III are obtained according to the process described in Preparation XI. Compound 70 was prepared from cyclopropylmethyl phenyl ketone. The latter compound was prepared from cyclopropylacetonitrile and phenylmagnesium bromide.

TABLE III

| Compound | $R_3$ | $R_5$ | $R_6$ |
|---|---|---|---|
| 66 | —$C_3H_7$ |  | ▲—$CH_3$ |

TABLE III-continued

HN(R₃)–CH(R₅)–R₆ structure

| Compound | R₃ | R₅ | R₆ |
|---|---|---|---|
| 67 | —C₃H₇ | cyclobutyl | cyclobutyl |
| 68 | —C₃H₇ | cyclopropyl-CH₃ | cyclopropyl-CH₃ |
| 69 | phenyl | cyclopropyl | cyclopropyl |
| 70 | —C₃H₇ | cyclopropyl-CH₂ | phenyl |

PREPARATION XII

N-(2,2-dicyclopropylethyl)propylamine (Compound 71)

This compound was prepared from 2,2-dicyclopropylacetaldehyde according to the process described in Preparation V.

PREPARATION XIII

N-(1-phenyl-4-pentenyl)propylamine (Compound 72)

Step A

Stir 0.48 ml of cyclopropylmethyl bromide, dissolved in 20 ml of ethyl ether, under argon at −70° C. and then add 3 ml of a solution of tert-butyllithium (1.7M in pentane).

Leave stirring for 30 minutes.

Step B

Proceed as described in Preparation VI, Step A, using benzaldehyde instead of 4-pyridinecarbaldehyde.

Step C

Add 730 mg of the imine obtained in Step B, dissolved in 2 ml of ethyl ether, slowly to the reaction solution obtained in Step A.

Allow the temperature to rise gradually to 0° C. and then add ammonium chloride solution dropwise.

The ether phase is separated from the aqueous phase, and the aqueous phase is extracted with ethyl ether. The ether phases are combined and extracted with twice 50 ml of 1N hydrochloric acid.

The aqueous phases are alkalinised with 1N sodium hydroxide solution and then extracted with 3 times 50 ml of methylene chloride.

The combined organic extracts are washed with water and with water saturated with sodium chloride, dried over anhydrous sodium sulphate and then evaporated to dryness to obtain an oil.

Yield: 81%

Proton nuclear magnetic resonance spectrum (solvent $CDCl_3$): 0.77–0.92 ppm, m, 3H; 1.27–1.93 ppm, m, 6H; 2.23–2.45 ppm, m, 2H; 3.57 ppm, t, 1H; 4.87–5.03 ppm, m, 2H; 5.60–5.82 ppm, m, 1H; 7.25–7.41 ppm, m, 5H.

PREPARATION XIV

N-(α-tert-butylbenzyl)propylamine (Compound 73)

Add 20 ml of ethyl ether to 3 ml of a solution of tert-butyllithium (1M in pentane) and leave stirring at −70° C. for approximately 30 minutes. Then add 730 mg of the imine whose preparation is described in Step B of Preparation XIII, dissolved in 2 ml of ethyl ether.

Increase the temperature gradually to 0° C. and then hydrolyse with aqueous ammonium chloride solution.

Separate the ether phase and extract the aqueous phase with ethyl ether. Combine the ether phases and extract with 100 ml of hydrochloric acid.

The acidic aqueous phases are then alkalinised with sodium hydroxide solution and thereafter extracted with methylene chloride.

The organic extract is then washed with water and thereafter with water saturated with sodium chloride, dried over anhydrous sodium sulphate and evaporated to dryness to obtain an oil.

Yield: 88%

Proton nuclear magnetic resonance spectrum (solvent $CDCl_3$): 0.84–1.0 ppm, m, 12H; 1.36–1.55 ppm, m, 2H; 2.29–2.46 ppm, m, 2H; 3.30 ppm, s, 1H; 7.19–7.35 ppm, m, 5H.

PREPARATION OF THE COMPOUNDS OF FORMULA III

PREPARATION XV

N-[cyclopropyl(4-pyridyl)methyl]-N-propylthiourea (Compound 74)

Step A

N'-benzoyl-N-[cyclopropyl(4-pyridyl)methyl]-N-propyl thiourea

Dissolve 0.88 g of ammonium thiocyanate in 6 ml of anhydrous acetone. Cool to 0° C. and add 1.1 ml of benzoyl chloride in 1 ml of acetone slowly. Bring to reflux for 10 minutes and then add 2 g of N-[cyclopropyl(4-pyridyl)methyl]propylamine (Compound 20) dissolved in 10 ml of acetone. After 1 hour of heating, evaporate off the solvent.

Take up the residue in water to obtain the expected compound in the form of white crystals.

Yield: 75% Melting point: 171° C.

Step B

Add 18 ml of 1N sodium hydroxide to 2.5 g of the compound obtained in the preceding step dissolved in 50 ml of ethanol. Bring the reaction medium to 80° C. for 48 hours, then add a further 10 ml of 1N sodium hydroxide and bring to 80° C. again for 24 hours.

After evaporating off the ethanol under vacuum, extract the resulting aqueous phase with methylene chloride.

Dry the organic phase and evaporate under vacuum.

Purify the residue by chromatography on a silica column, using a mixture of methylene chloride and methanol (98:2 V/V) as eluent.

Yield: 68% Melting point: Oil

Proton nuclear magnetic resonance spectrum (solvent $CDCl_3$): 0.85 ppm, t, 3H; 0.54–1.25 ppm, m, 8H; 1.78 ppm, m, 2H; 2.84–3.35 ppm, m, 2H; 6.03 ppm, d, 1H; 6.19 ppm, s, 2H; 7.42 ppm, d, 2H; 8.58 ppm, dd, 2H.

Other compounds (Compounds 75 to 113)

The thiourea derivatives shown in Table IVa and IVb are obtained according to the process described for N-[cyclopropyl(4-pyridyl)methyl]-N-propylthiourea, using the appropriate amines whose preparation is described above (Preparation of the compounds of formula VII), or using commercially available amines.

TABLE IVa

(III)

| Compound | $R_3$ | $R_5$ | $R'_6$ |
|---|---|---|---|
| 75 | —$C_3H_7$ |  |  |
| 76 | —$C_3H_7$ | 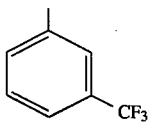 |  (3-$CF_3$-phenyl) |
| 77 | —$C_3H_7$ | 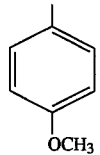 |  (4-$OCH_3$-phenyl) |
| 78 | —$C_3H_7$ | 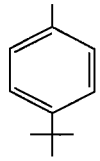 |  (4-t-butyl-phenyl) |
| 79 | —$C_3H_7$ | 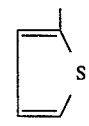 | 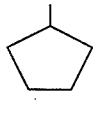 (thienyl) |
| 80 | —$C_3H_7$ | 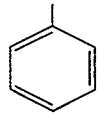 (cyclopentyl) |  |
| 81 | —$C_3H_7$ | 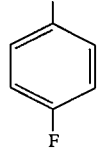 |  (4-F-phenyl) |
| 82 | —$C_3H_7$ | 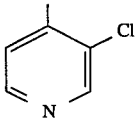 |  (3-Cl-pyridyl) |
| 83 | —$C_3H_7$ | 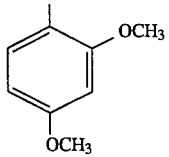 | (2,4-di-$OCH_3$-phenyl) |

TABLE IVa-continued
$$\underset{H_2N}{\overset{S}{\underset{\|}{C}}}-\underset{\underset{R_5}{|}}{\overset{R_3}{\underset{|}{N}}}-\underset{\underset{R_5}{|}}{\overset{H}{\underset{|}{C}}}-R'_6 \quad (III)$$
| Compound | R₃ | R₅ | R'₆ |
|---|---|---|---|
| 84 | —C₃H₇ | 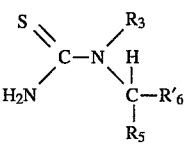 |  |
| 85 | —C₃H₇ | 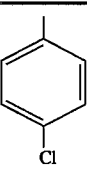 |  |
| 86 | —C₃H₇ | 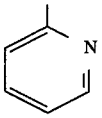 |  |
| 87 | —C₃H₇ | —CH₃ | 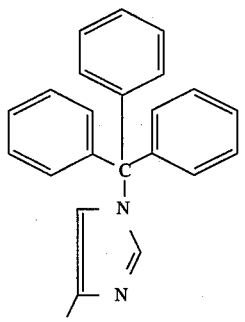 |
| 88 | —C₃H₇ | 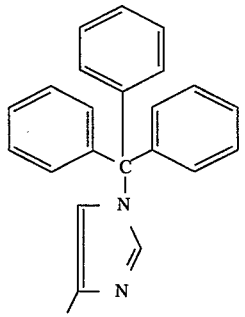 |  |
| 89 | —C₃H₇ |  | 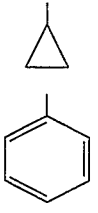 |
| 90 | —C₃H₇ | 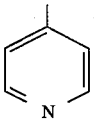 |  |
| 91 | —C₃H₇ | —CH₃ |  |

TABLE IVa-continued
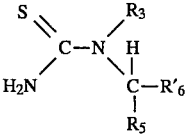
(III)
| Compound | R₃ | R₅ | R'₆ |
|---|---|---|---|
| 92 | H | —CH₃ | 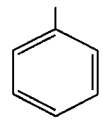 |
| 93 | —C₃H₇ |  | 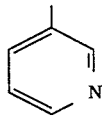 |
| 94 | —C₃H₇ |  | 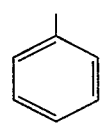 |
| 95 | —C₃H₇ |  | 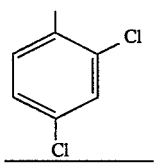 |
| 96 | —C₃H₇ |  | 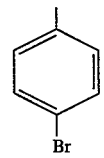 |
| 97 | —C₃H₇ |  | 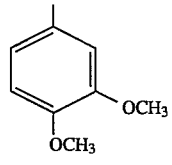 |
| 98 | —C₃H₇ |  | 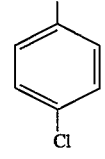 |
| 99 | —C₃H₇ |  | 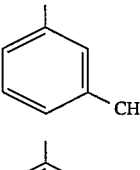 |
| 100 | —C₃H₇ |  | 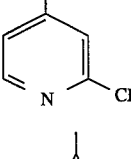 |
| 101 | —C₃H₇ | —CH₃ |  |

TABLE IVa-continued
$$\underset{H_2N}{\overset{S}{\underset{\|}{C}}}-\underset{\underset{R_5}{\overset{|}{C}}-R'_6}{\overset{R_3}{\underset{|}{N}}\overset{H}{\underset{|}{}}}$$ (III)
| Compound | R$_3$ | R$_5$ | R'$_6$ |
|---|---|---|---|
| 102 | —C$_3$H$_7$ |  | 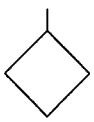 |
| 103 | —C$_3$H$_7$ | —(CH$_2$)$_2$—CH=CH$_2$ | 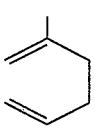 |
| 104 | —C$_3$H$_7$ | 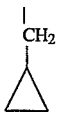 | 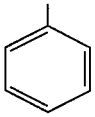 |
| 105 | —C$_3$H$_7$ |  —CH$_3$ |  —CH$_3$ |
| 106 | —C$_3$H$_7$ | 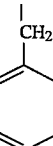 |  |
| 107 | —C$_3$H$_7$ | H$_3$C—$\underset{\underset{CH_3}{\overset{|}{C}}}{\overset{|}{}}$—CH$_3$ | 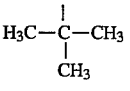 |
| 108 | —C$_3$H$_7$ | 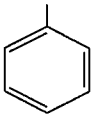 |  —CH$_3$ |
| 109 | —C$_3$H$_7$ |  | 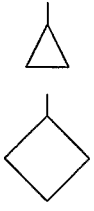 |
| 110 | —C$_3$H$_7$ | 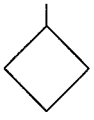 |  |
| 111 |  | 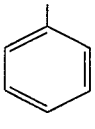 | 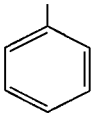 |
| 112 | 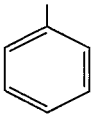 | 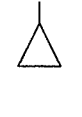 | |

TABLE IVa-continued

| Compound | R₃ | R₅ | R'₆ |
|---|---|---|---|
| 113 | C₃H₇ | 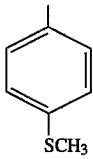 |  |
| 114 | C₃H₇ | 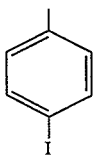 |  |

TABLE IVb

| Compound | R₃ | R₅ | R'₆ |
|---|---|---|---|
| 115 | —C₃H₇ | 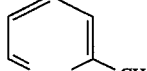 | 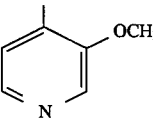 |

PREPARATION XVI

N-[1-(3-chloro-4-pyridyl)ethyl]-N-propylthiourea (Compound 116)

Step A

N'-benzoyl-N-[1-(3-chloro-4-pyridyl)ethyl]-N-propylthiourea

Prepare this compound according to the process described in Step A of Preparation XV, from 1.14 g of ammonium thiocyanate, 1.74 ml of benzoyl chloride and 2.7 g of N-[1-(3-chloro-4-pyridyl)ethyl]propylamine (Compound 22).

Step B

Add 6 ml of 32% hydrochloric acid to 1.18 g of the compound obtained in Step A. Bring the reaction medium to 80° C. for one hour, then cool and add water. Extract with methylene chloride and discard the organic phase. Alkanilise the aqueous phase with sodium carbonate and extract with methylene chloride. Dry the organic phase and evaporate under vacuum. Purify the residue by chromatography on a silica column, using a mixture of methylene chloride and methanol (98:2 V/V) as eluent.

Yield: 98% Melting point: Oil.

Proton nuclear magnetic resonance spectrum (solvent CDCl₃): 0.73 ppm, t, 3H; 1.05–1.66 ppm, m, 2H; 1.63 ppm, d, 3H; 3.16 ppm, t, 2H; 5.87 ppm, s, 2H; 6.77 ppm, q, 1H; 7.29 ppm, d, 1H; 8.53 ppm, d, 1H; 8.59 ppm, s, 1H.

Other compounds (Compounds 117 to 121)

The thiourea derivatives shown in Table V are obtained according to the process described for N-[1-(3-chloro-4-pyridyl)ethyl]-N-propylthiourea.

TABLE V

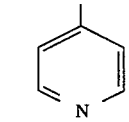

| Compound | R₃ | R₅ | R'₆ |
|---|---|---|---|
| 117 | —C₃H₇ | —CH₃ |  |
| 118 | —C₃H₇ | —CH₃ | 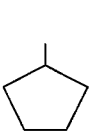 |
| 119 | —C₃H₇ | —C₂H₅ | |
| 120 | —C₃H₇ | | |
| 121 | —C₃H₇ | | |

PREPARATION XVII

N-cyclopropylmethyl-N-[1-(4-pyridyl)ethyl]thiourea (Compound 122)

Step A

N'-pivaloyl-N-cyclopropylmethyl-N-[1-(4-pyridyl)ethyl]thiourea

Dissolve under argon 2.9 g of potassium thiocyanate in 30 mol of acetone in a 100-ml three-necked flask. Cool to 0° C. and add 3.4 ml of pivaloyl chloride dropwise. Stir at 0° C. for 5 hours and then add 4.8 g of N-(cyclopropylmethyl)-1-(4-pyridyl)ethylamine (Compound 61). Stir at room temperature overnight. Evaporate to dryness. The residue is taken up in water and extracted into methylene chloride. Dry over anhydrous sodium sulphate and evaporate to dryness. The powder obtained is washed with hexane and filtered off.

Yield: 75%

Proton nuclear magnetic resonance spectrum (solvent $CDCl_3$): 0.02–0.07 ppm, m, 2H; 0.4–0.5 ppm, m, 2H; 0.96 ppm, m, 1H; 1.28 ppm, s, 9H; 1.77 ppm, d, 3H; 2.90 ppm, dd, 2H; 3.4 ppm, m, 1H; 6.5 ppm, s, 1H; 7.4 ppm, m, 2H; 8.61 ppm, d, 2H.

Step B

Dissolve 2 g of the product obtained in the preceding step in 15 ml of 32% hydrochloric acid and heat to 70° C. for one hour. Cool and alkalinise with saturated aqueous sodium bicarbonate solution. Extract with ethyl acetate, dry over anhydrous sodium sulphate and evaporate to dryness. Take up the residue in a mixture of hexane and ethyl acetate (8:2 V/V).

Filter to isolate white crystals.

Yield: 87%

Other compounds (Compounds 123 to 129)

The thioureas shown in Table VI were obtained according to the process described in Preparation XVII.

TABLE VI (III)

| Compound | $R_3$ | $R_5$ | $R'_6$ |
|---|---|---|---|
| 123 | $-C_3H_7$ | $-CH_3$ | 4-pyridyl |
| 124 | $-C_3H_7$ | $-CH_3$ | 3-pyridyl |
| 125 | $-CH_2CH(CH_3)_2$ | $-CH_3$ | 4-pyridyl |
| 126 | $-CH_3$ | $-CH_3$ | 2-methyl-3-pyridyl |
| 127 | $-C_2H_5$ | $-CH_3$ | 4-pyridyl |
| 128 | cyclopropyl | $-CH_3$ | 3-pyridyl |
| 129 | $-C_3H_7$ | $-CH_3$ | 2-chloro-4-pyridyl |

EXAMPLES

Example 1

4-(2,4-dichlorophenyl)-5-methyl-2-[N-(α-cyclopropylbenzyl)-N-propylamino]thiazole To 1.35 g of N-(α-cyclopropylbenzyl)-N-propylthiourea (Compound 75) in 35 ml of ethanol, add 546 mg of triethylamine, then slowly 1.52 g of 2-bromo-1-(2,4-dichlorophenyl)-1-propanone (Compound 15). After 3 hours of heating at 75° C., remove the precipitate formed by filtration. The ethanolic solution is evaporated to dryness. Take up the residue in ethyl ether and wash with water until bromide ions have disappeared. Dry the organic phase over anhydrous sodium sulphate and then evaporate to dryness. Purify the residue on a silica column, using a mixture of cyclohexane and ethyl acetate (10:1 V/V) as eluent, to obtain the expected product. Recrystallise in acetonitrile (white crystals).

Yield: 79% Melting point: 78° C.–81° C.

The proton nuclear magnetic resonance spectrum is shown in Table VII.

Example 2

4-(2,4-dichlorophenyl)-5-methyl-2-{N-[cyclopropyl(4-pyridyl)methyl]-N-propylamino}thiazole This compound was prepared according to the process described in Example 1, starting with 1.2 g of N-[cyclopropyl(4-pyridyl)methyl]-N-propylthiourea (Compound 74) and 1.52 g of 2-bromo-1-(2,4-dichlorophenyl)-1-propanone Compound 15). The product was purified on a silica column, using a mixture of methylene chloride and methanol (98:2 V/V) as eluent.

Oil. Yield: 78%

From this base, using the appropriate acids dissolved in ethanol, the following salts were obtained:

Hemifumarate: melting point: 98° C.

Hydrochloride: melting point: 68° C.

Disulphate: melting point: 186° C.

The proton nuclear magnetic resonance spectrum of this product is shown in Table VII.

Examples 3 to 40

According to the process described in Example 1, the compounds of Examples 3–40 were obtained using the appropriate bromo ketones and thiourea derivatives. Their spectral characteristics are shown in Table VII.

Example 41

4-(2,4-dichlorophenyl)-5-methyl-2-[N-(α-methylbenzyl)-N-(cyclopropylmethyl)amino]thiazole At 0° C., add 0.5 g of 4-(2,4-dichlorophenyl)-5-methyl-2-[N-(α-methylbenzyl)amino]thiazole (prepared from Compound 92 and Compound 15 according to the process described in Example 1), dissolved in 5 ml of anhydrous tetrahydrofuran, and 66 mg of sodium hydride. After 30 minutes of stirring at room temperature, run in 0.67 ml of cyclopropylmethyl bromide dropwise. Leave for eight hours under reflux, cool and dilute the reaction medium with methylene chloride, then pour it onto ice.

Dry and evaporate the organic phase to obtain an oil, which is then purified on a silica column, using a mixture of cyclohexane and ethyl acetate (40:1 V/V) as eluent.

Yield: 57%

The proton nuclear magnetic resonance spectrum of 4-(2, 4-dichlorophenyl)-5-methyl-2-[N-(α-methylbenzyl)-N-(cyclopropylmethyl)amino]thiazole is shown in Table VII.

Example 42

4-(2,4-dichlorophenyl)-2-{N-[cyclopropyl(4-imidazolyl)methyl]-N-propylamino}-5-methylthiazole
Step A
4-(2,4-dichlorophenyl)-5-methyl-2-{N-]cyclopropyl(1-trityl-4-imidazolyl)methyl]-N-propylamino}thiazole This compound was prepared from N-[cyclopropyl(1-trityl-4-imidazolyl)methyl]-N-propylthiourea (Compound 86) and 2-bromo-1-(2,4-dichlorophenyl)-1-propanone (Compound 15) according to the process described in Example 1.
Step B Add 45 ml of 2N hydrochloric acid to 3 g of the product obtained in the preceding step dissolved in 45 ml of acetone. After a night at room temperature, evaporate off the acetone, wash the remaining aqueous phase with ethyl ether and then add sodium bicarbonate. Extract the precipitate formed with 3 times 100 ml of ethyl acetate. Wash the organic phase with saturated aqueous sodium chloride solution and then dry over anhydrous sodium sulphate. Evaporate under vacuum to obtain 4-(2,4-dichlorophenyl)-5-methyl-2-{N-] cyclopropyl(4-imidazolyl)methyl]-N-propylamino}thiazole in the form of a white powder.

Yield: 90% Melting point: 83° C.

The proton nuclear magnetic resonance spectrum of this product is shown in Table VII.

Example 43

4-(2,4-dichlorophenyl)-5-methyl-2-{N-[1-(4-imidazolyl)ethyl]-N-propylamino}thiazole This compound was prepared according to the process described in Example 42, and using N-[1-(1-trityl-4-imidazolyl)ethyl]-N-propylthiourea (Compound 87) in Step A as a thiourea derivative. The proton nuclear magnetic resonance spectrum of this product is shown in Table VII.

Example 44

4-(2,4-dichlorophenyl)-5-methyl-2-{N-[cyclopropyl(1-benzyl-4-imidazolyl)methyl]-N-propylamino}thiazole Add 320 mg of potassium carbonate to 492 mg of the compound of Example 42, dissolved in 10 ml of dimethylformamide, and then, at 0° C., slowly add 0.12 ml of benzyl chloride dissolved in 1 ml of dimethylformamide. Leave to act for 3 hours at approximately 60° C. and then 3 hours at 80° C. Add water to form a precipitate. Extract with ethyl acetate. Wash the organic phase with saturated sodium chloride solution. Evaporate to dryness and purify the residue by chromatography on a silica column, using a mixture of cyclohexane and ethyl acetate (2:1 V/V) as eluent.

Yield: 67%

Add an appropriate quantity of 0.1N hydrochloric acid, dissolved in isopropanol, to form the corresponding dihydrochloride.

Melting point: 115° C.

The proton nuclear magnetic resonance spectrum of 4-(2, 4-dichlorophenyl)-5-methyl-2-{N-[cyclopropyl(1-benzyl-4-imidazolyl)methyl] -N-propylamino)thiazole is shown in Table VII.

Example 45

4-(2,4-dichlorophenyl)-5-methyl-2-{N-[cyclopr opyl(1-methyl-4-imidazolyl)methyl]-N-propylamino} thiazole Add 570 mg of powdered potassium hydroxide to 856 mg of the compound of Example 42 dissolved in 10 ml of acetone. Stir for 5 minutes and then add 0.14 ml of methyl iodide. After 15 minutes at room temperature, dilute the reaction mixture in 100 ml of dichloromethane, and then wash with water and with water saturated with sodium chloride. Dry the organic phase over sodium sulphate, evaporate to dryness and then subject the residue to chromatography on a silica column, using a mixture of cyclohexane and ethyl acetate (1:1 V/V) as eluent.

In this way, 4-(2,4-dichlorophenyl)-5-methyl-2-{N-[cyclopropyl(1-methyl-4-imidazolyl)methyl] -N-propylamino}thiazole and 4-(2,4-dichlorophenyl)-5-methyl-2-{N-[cyclopropyl(3-methyl-4-imidazolyl)methyl]-N-propylamino}thiazole (37:63) are separated.

Yield: 33%

Example 46

5-bromo-4-(2,4-dichlorophenyl)-2-{N-[propyl-N-]1-(4-pyridyl)ethyl]amino}thiazole Dissolve 1 g of 4-(2,4-dichlorophenyl)-2-{N-]propyl-N-[1-(4-pyridyl)ethyl]amino}thiazole, the compound of Example 25, in 20 ml of methylene chloride. Add 0.15 ml of bromine. Stir overnight. Evaporate to dryness. Dissolve the residue in a minimum amount of isopropanol and precipitate with ethyl ether. Filter and wash with ethyl ether, then dissolve in 5% aqueous potassium carbonate solution. Extract with ethyl acetate, dry over anhydrous magnesium sulphate and evaporate to dryness to obtain the expected product in the form of an oil.

Yield: 80%

The proton nuclear magnetic resonance spectrum of 5-bromo-4-(2,4-dichlorophenyl)-2-{N-propyl-N-[1-(4-pyridyl)ethyl]amino}thiazole is shown in Table VII.

Example 47

4-(2,4-dichlorophenyl)-5-methyl-2-[N-(dicyclopropylmethyl)-N-propylamino]thiazole To 1 g of N-(dicyclopropylmethyl)-N-propylthiourea (Compound 88) dissolved in 25 ml of anhydrous ethanol, add 0.54 ml of triethylamine, then slowly 1 g of 2-bromo-1-(2,4-dichlorophenyl)-1-propanone (Compound 15). After two hours of heating under reflux of the ethanol, evaporate to dryness. Take up the residue in methylene chloride and wash with water until bromide ions have been removed completely. Dry the organic phase over anhydrous sodium sulphate and then evaporate to dryness. Purify the residue on a silica column, using a mixture of cyclohexane and ethyl acetate (20:1 V/V) as eluent, to obtain the expected product in the form of an oil.

Yield: 88%

The proton nuclear magnetic resonance spectrum is shown in Table VII.

To obtain the corresponding sulphate, add an appropriate quantity of 1M sulphuric acid in ethanol to this base.

Melting point: 140° C.

Example 48

4-(2,4-dichlorophenyl)-5-methyl-2-{N-[cyclopentyl(cyclopropyl)methyl]-N-propylamino}thiazole This compound was obtained according to the process described in Example 47, but using N-[cyclopentyl(cyclopropyl)methyl]-N-propylthiourea (Compound90) as a thiourea derivative. In the purification on a silica column, use a mixture of cyclohexane and ethyl acetate (10:1 V/V) as eluent.

Yield: 95%

The proton nuclear magnetic resonance spectrum is shown in Table VII.

Example 49

4-(2,4-dichlorophenyl)-5-formyl-2-{N-propyl-N-[1-(4-pyridyl)ethyl]amino}thiazole Introduce 3 ml of dimethylformamide into a 100-ml round-bottomed flask. Cool to −30° C. and add 0.45 ml of oxalyl chloride dropwise. Stir for 30 minutes at 0° C. and then allow the temperature to increase. Then add 0.5 g of the compound of Example 25. Stir for 6 hours. Leave to act overnight. Add water and alkalinise with 1N sodium hydroxide solution. Filter off the precipitate formed to obtain a gum. Dissolve in a minimum amount of ethyl ether and add hexane until a slight cloudiness is obtained. Leave to precipitate, filter and wash with hexane to obtain the expected product in the form of orange crystals.

Yield: 75% Melting point: 114° C.

The proton nuclear magnetic resonance spectrum of 4-(2,4-dichlorophenyl)-5-formyl-2-{N-propyl-N-[1-(4-pyridyl)ethyl]amino}thiazole is shown in Table VII.

Example 50

4-(2,4-dichlorophenyl)-5-hydroxymethyl-N-[1-(4-pyridyl)ethyl]amino}thiazole

Cool a solution containing 1.1 g of the compound of Example 49 in 20 ml of anhydrous methanol in an ice bath, and add 0.2 g of sodium borohydride in small amounts. Leave to react at room temperature and then evaporate off the solvent. Extract the residue with ethyl acetate. Dry the organic phase over anhydrous sodium sulphate. Evaporate to dryness and dissolve the residue in ethyl ether.

Precipitate with hexane to obtain the expected product in the form of an orange powder.

Yield: 72% Melting point: 113° C.

The proton nuclear magnetic resonance spectrum of this product is shown in Table VII.

Example 51

4-(2,4-dichlorophenyl)-5-methyl-2-{N-(2-propenyl)-N-[1-(4-pyridyl)ethyl]amino}thiazole Dissolve under argon 2.0 g of 4-(2,4-dichlorophenyl)-5-methyl-2-{N-[1-(4-pyridyl)ethyl] amino}thiazole (prepared from N-[1-(4-pyridyl)ethyl]thiourea and 2-bromo-1-(2,4-dichlorophenyl)-1-propanone (compound 15), according to the process described in Example 1) in 20 ml of anhydrous tetrahydrofuran in a 100-ml three-necked flask.

Add 0.4 g of lithium amide and stir for 1 hour at 50° C. Add 0.43 g of allyl bromide and heat to 60° C. for 48 hours.

Evaporate to dryness and then add 10 ml of 10% aqueous sodium hydroxide solution. Extract with ethyl acetate, dry the organic phase over anhydrous sodium sulphate and evaporate to dryness. Purify the residue using a mixture of ethyl acetate and hexane (75:25 V/V) as eluent, to obtain the expected product in the form of an oil.

Yield: 20%

The proton nuclear magnetic resonance spectrum is shown in Table VII.

To obtain the oxalate of 4-(2,4-dichlorophenyl)-5-methyl-2-{N-(2-propenyl)-N-[1-(4 -pyridyl)ethyl]amino}thiazole, dissolve 0.4 g of base in a minimum amount of isopropanol and add 0.18 g of oxalic acid previously dissolved in isopropanol.

Evaporate to dryness and recrystallise, first in a mixture of isopropanol and ethyl ether (50:50 V/V), and then in isopropanol.

Melting point: 150° C.

Example 52

4-(4-chloro-2-hydroxyphenyl)-5-methyl-2-{N-propyl-N-[1-(4-pyridyl)ethyl]amino}thiazole Bring to reflux for 24 hours 700 mg of 4-(4-chloro-2-methoxyphenyl)-5-methyl-2-{N-propyl-N-[1-(4-pyridyl)ethyl]amino}thiazole, the compound of Example 22, dissolved in 30 ml of concentrated hydrobromic acid. Evaporate to dryness and take up the residue in Water saturated with potassium carbonate. Extract with methylene chloride and then evaporate off the organic solvent. Purify the residue by chromatography on a silica column, using a mixture of ethyl acetate and methanol (9:1 V/V) as eluent, to obtain the expected product in the form of an oil.

Yield: 67%

The proton nuclear magnetic resonance spectrum of the compound of this example is shown in Table VII.

Example 53

4-(2-chloro-4-hydroxyphenyl)-5-methyl-2-{N-propyl-N-[1-(4-pyridyl)ethyl]amino}thiazole This compound was obtained from the compound of Example 27 according to the process described in Example 52.

The proton nuclear magnetic resonance spectrum of 4-(2-chloro-4-hydroxyphenyl)-5-methyl-2-{N-propyl-N-[1-(4-pyridyl)ethyl]amino}thiazole is shown in Table VII.

Examples 54 to 88

According to the process described in Example 1, the compounds of Examples 54 to 87 were obtained using the appropriate bromoacetone and thiourea derivatives.

Their spectral characteristics are shown in Table VII.

Example 89

5-bromo-4-(2,4-dichlorophenyl)-2-[N-(α-cyclopropylbenzyl)-N-propylamino]thiazole This compound was prepared from 4-(2,4-dichlorophenyl)-2-[N-(α-cyclopropylbenzyl)-N-propylamino]thiazole, the compound of Example 82, and according to the process described in Example 46.

The proton nuclear magnetic resonance spectrum is shown in Table VII.

Example 90

4-(2,4-dichlorophenyl)-5-iodo-2-[N-(α-cyclopropylbenzyl)-N-propylamino]thiazole

Dissolve 496 mg of 5-bromo-4-(2,4-dichlorophenyl)-2-[N-(α-cyclopropylbenzyl)-N-propylamino]thiazole, the compound of Example 89, in 20 ml of ethyl ether and cool this solution to −70° C., then slowly add 0.8 ml of a solution of tert-butyllithium (1.5N in pentane). Then run in slowly 305 mg of iodine dissolved in 20 ml of tetrahydrofuran. Bring the temperature back slowly to 0° C., hydrolyse with saturated aqueous sodium chloride solution and wash with thiosulphate solution.

Purify as described in Example 1 to obtain the expected product.

The proton nuclear magnetic resonance spectrum of 4-(2,4-dichlorophenyl)-5-iodo-2-[N-(α-cyclopropylbenzyl)-N-propylamino]thiazole is shown in Table VII.

Example 91

4-(2-chloro-4-iodophenyl)-5-methyl-2-[N-(α-cyclopropylbenzyl)-N-propylamino]thiazole This compound was prepared from N-(α-cyclopropylbenzyl)-N-propylthiourea (Compound 75) and 2-bromo-1-(2-chloro-4-iodophenyl)-1-propanone (Compound 18) according to the process described in Example 1.

The proton nuclear magnetic resonance spectrum of this compound is shown in Table VII.

Example 92

4-(2,4-dichlorophenyl)-5-methyl-2-[N-(2,2-dicyclopropylethyl)-N-propylamino]thiazole This compound was obtained from 2-bromo-1-(2,4-dichlorophenyl)-1-propanone (Compound 15) and N-(2,2-dicyclopropylethyl)-N-propylthiourea (Compound 115) according to the process described in Example 1.

Melting point: gum

Proton nuclear magnetic resonance spectrum (solvent CDCl$_3$): 0.0–0.7 ppm, m, 11H; 0.9 ppm, m, 3H; 1.4–1.9 ppm, m, 2H; 2.10 ppm, s, 3H; 3.3–3.5 ppm, m, 4H; 7.1–7.4 ppm, m, 3H.

Example 93

4-(2,4-dichlorophenyl)-5-methyl-2-[N-(α-cyclopropylbenzyl)-N-propylamino]thiazole (+) isomer and 4-(2,4-dichlorophenyl)-5-methyl-2-[N-(α-cyclopropylbenzyl)-N-propylamino]thiazole (−) isomer The two stereoisomers of 4-(2,4-dichlorophenyl)-5-methyl-2-[N-(α-cyclopropylbenzyl)-N-propylamino]thiazole (compound of Example 1), were obtained according to two methods.

METHOD A

Step A
α-cyclopropylbenzylamine

Stir 100 g of cyclopropyl phenyl ketone in 2000 ml of methanol with 500 g of previously dried ammonium acetate and 50 g of sodium cyanoborohydride at 50° C. for 4 days under argon in the presence of 4 Å molecular sieve. After cooling, filter off the molecular sieve and then add concentrated hydrochloric acid to take the pH to 2. Evaporate the solution to dryness under vacuum and take up the residue in water. The aqueous phase is washed with ethyl ether and then alkalinised by adding concentrated potassium hydroxide solution so that the pH is above 10. Extract twice with methylene chloride, wash with saturated sodium chloride solution, dry over anhydrous magnesium sulphate and then concentrate under vacuum to obtain α-cyclopropylbenzylamine, which is used without any further purification in the next step.

Yield: 76%

Step B
α-cyclopropylbenzylamine (+) isomer and α-cyclopropylbenzylamine (−) isomer Add 80.6 g of L(+)-tartaric acid to 275 ml of absolute ethanol and bring to reflux. Then add dropwise 79 g of the α-cyclopropylbenzylamine obtained in the preceding step. When the addition is complete, cool the reaction medium slowly, and thus obtain crystals. Recrystallise these crystals 5 times in absolute ethanol. The optical purity of the amine obtained is monitored by gas chromatography with Mosher's reagent. α-Cyclopropylbenzylamine (+) isomer is thereby obtained in the form of a tartaric salt with an optical purity of greater than 96%.

Yield: 25% Melting point: 150° C. $[\alpha]_{365}^{20}$=+138.6° (C=0.56% in methanol)

α-Cyclopropylbenzylamine (+) isomer is obtained from the salt after solubilisation in water, alkalinisation of the solution, extraction with methylene chloride, drying over anhydrous magnesium sulphate and evaporation under vacuum.

$[\alpha]_{365}^{20}$=+159.6° (C=0.99% in methanol)

Combine the ethanolic solutions from the above resolution and evaporate to dryness. Take up the residue in water, alkalinise, extract with methylene chloride, dry over anhydrous magnesium sulphate and evaporate to dryness. Salify with D(−)-tartaric acid, applying the salification and resolution method described above. After recrystallisations in ethanol, the tartaric salt of α-cyclopropylbenzylamine (−) isomer is obtained with an optical purity of greater than 96%.

Yield: 20% Melting point: 151° C. $[\alpha]_{365}^{20}$=−141.9° (C=0.94% in methanol)

Step C
4-(2,4-dichlorophenyl)-5-methyl-2-[N-(α-cyclopropylbenzyl)amino]thiazole (−) isomer and 4-(2,4-dichlorophenyl)-5-methyl-2-[N-(α-cyclopropylbenzyl)amino]thiazole (+) isomer Proceed as described in Preparation XV, using α-cyclopropylbenzylamine (+) isomer as an amine to obtain N-(α-cyclopropylbenzyl)thiourea (+) isomer. Then react the latter compound with 2-bromo-1-(2,4-dichlorophenyl)-1-propanone (Compound 15) according to the process described in Example 1 to obtain 4-(2,4-dichlorophenyl)-5-methyl-2-[N-(α-cyclopropylbenzyl)amino]thiazole (−) isomer.

Overall yield: 62% $[\alpha]_{365}^{20}$=−72.8° (C=0.82% in methanol)

4-(2,4-Dichlorophenyl)-5-methyl-2-[N-(α-cyclopropylbenzyl)amino]thiazole (+) isomer was prepared according to the process described above, using α-cyclopropylbenzylamine (−) isomer as the starting amine.

Step D

Then dissolve 1.18 g of 4-(2,4-dichlorophenyl)-5-methyl-2-[N-(α-cyclopropylbenzyl)amino]thiazole (−) isomer in 35 ml of anhydrous dimethylformamide and add at 0° C. 145 mg of sodium hydride and then, after the gaseous evolution has ceased, 370 mg of propyl bromide. Heat for 2 hours and 30 minutes to 75° C. Evaporate to dryness and hydrolyse with water. The aqueous phase is extracted with ethyl acetate. The organic phase thereby obtained is washed with water saturated with sodium chloride solution, dried over anhydrous magnesium sulphate and then evaporated under vacuum to obtain a residue, which is purified on a silica column, using a mixture of cyclohexane and ethyl acetate (20:1 V/V) as eluent.

4-(2,4-Dichlorophenyl)-5-methyl-2-[N-(α-cyclopropylbenzyl)-N-propylamino]thiazole (−) isomer is obtained in the form of a gummy product. $[\alpha]_{365}^{20}=-452°$ (C=1.0% in methanol)

From this base, and using the appropriate acids dissolved in ethanol, the following salts were obtained:

Hydrochloride: Melting point: 66.5° C. $[\alpha]_{365}^{20}=-452°$ (C=0.62% in methanol) $[\alpha]_D^{20}=-81.9°$ (C=0.62% in methanol) para-Toluenesulphonate: Melting point: 72° C.

4-(2,4-Dichlorophenyl)-5-methyl-2-[N-(α-cyclopropylbenzyl)-N-propylamino]thiazole (+) isomer was prepared according to the process described above, using 4-(2,4-dichlorophenyl)-5-methyl-2-[N-(α-cyclopropylbenzyl)amino]thiazole (+) isomer.

The corresponding hydrochloride was prepared by reacting 4-(2,4-dichlorophenyl)-5-methyl-2-[N-(α-cyclopropylbenzyl)-N-propylamino]thiazole (+) isomer with a solution of hydrochloric acid in methanol.

Melting point: 71° C. $[\alpha]_{365}^{20}=+439.7°$ (C=0.69% in methanol) $[\alpha]_D^{20}=+78.5°$ (C=0.69% in methanol)

METHOD B

Step A

α-Cyclopropylbenzylamine (+) isomer and α-cyclopropylbenzylamine (−) isomer

Prepare (E,Z)-(cyclopropyl phenyl ketone oxime) according to the process described in Org. Synth. Coll. Vol II, p. 70, A. H. Blatt, J. Willey and Sons Inc. Edt. New York, London, Sydney, Copyright 1943.

The mixture thereby obtained contains 76% of E isomer and 24% of Z isomer. Recrystallise several times in methanol, or isomerise in an acid medium according to the process below.

Dissolve 2 g of (E,Z)-(cyclopropyl phenyl ketone oxime) in 20 ml of anhydrous ethyl ether and saturate with gaseous hydrochloric acid. Filter off the precipitate obtained and then add 50 ml of 10% aqueous $K_2CO_3$ solution. Extract the solid with methylene chloride. Wash the organic phase with water, dry over anhydrous magnesium sulphate and evaporate to dryness to obtain (E)-(cyclopropyl phenyl ketone oxime).

Purity: 98%

Add 1.61 g of the oxime thereby obtained, dissolved in 10 ml of anhydrous dimethylformamide, to a solution containing 276 mg of sodium hydride in 10 ml of anhydrous dimethylformamide. After one hour of stirring at room temperature, add 0.75 ml of methyl iodide. After 4 hours of stirring, pour the reaction medium onto ice. Extract with ethyl acetate, dry, evaporate under vacuum and purify on a silica column, using a mixture of cyclohexane and ethyl acetate (40:1 V/V) as eluent, to obtain (E)-(cyclopropyl phenyl ketone oxime) methyl ether. To 385 mg of norephedrine (−) isomer, dissolved in 5 ml of anhydrous tetrahydrofuran and at −30° C., then add 8.6 ml of 1M borane-tetrahydrofuran complex and thereafter 300 mg of (E)-(cyclopropyl phenyl ketone oxime) methyl ether dissolved in 3 ml of anhydrous tetrahydrofuran. Bring to reflux for 2 hours 30 minutes and then, at 0° C., add 10 ml of water and 10 ml of 20% sodium hydroxide. Bring to reflux for 1 hour 30 minutes. After cooling, extract with methylene chloride, dry the organic phase and evaporate to dryness. Take up the residue in an excess of methanol and bring to reflux for 5 hours, then evaporate to dryness and purify on a silica column, using a mixture of methylene chloride and methanol (96:4 V/V) as eluent.

α-Cyclopropylbenzylamine (+) isomer is thereby obtained with an optical purity of greater than 90%.

Yield: 40%

α-Cyclopropylbenzylamine (−) isomer is obtained according to the process described above, but using norephedrine (+) isomer as the chiral agent in the reduction of (E)-(cyclopropyl phenyl ketone oxime) methyl ether.

Steps B and C

Then proceed as described in Method A, Steps C and D, to obtain 4-(2,4-dichlorophenyl)-5-methyl-2-[N-(α-cyclopropylbenzyl)-N-propylamino]thiazole (+) isomer and 4-(2,4-dichlorophenyl)-5-methyl-2-[N-(α-cyclopropylbenzyl)-N-propylamino]thiazole (−) isomer.

TABLE VII

| EXAMPLE | R₁ | R₂ | R₃ | R₅ | R₆ | NMR SPECTRUM (SOLVENT) |
|---|---|---|---|---|---|---|
| 1 | 2,4-dichlorophenyl | $-CH_3$ | $-C_3H_7$ | cyclopropyl | phenyl | (CDCl₃)Base 0.40 ppm, m, 1H; 0.62 ppm, m, 2H; 0.76 ppm, m, 4H; 1.35 ppm, m, 1H; 1.65 ppm, q, 2H; 2.09 ppm, s, 3H; 3.16 ppm, m, 2H; 4.62 ppm, d, 1H; 7.15–7.30 ppm, m, 5H; 7.37–7.44 ppm, m, 3H. |
| 2 | 2,4-dichlorophenyl | $-CH_3$ | $-C_3H_7$ | cyclopropyl | 4-pyridyl | (CDCl₃)Disulphate salt 0.47–0.94 ppm, m, 4H; 0.88 ppm, t, 3H; 1.17 ppm, m, 1H; 1.76 ppm, m, 2H; 2.16 ppm, s, 3H; 3.10–3.29 ppm, dd, 2H; 4.74 ppm, d, 1H; 7.35–7.45 ppm, m, 5H; 8.54 ppm, d, 2H. |
| 3 | 2,4-dichlorophenyl | $-CH_3$ | $-C_3H_7$ | cyclopropyl | 3-(trifluoromethyl)phenyl | (CDCl₃)Base 0.40–1.10 ppm, m, 7H; 1.5 ppm, m, 1H; 1.85 ppm, m, 2H; 2.20 ppm, s, 3H; 3.3 ppm, m, 2H; 4.97 ppm, d, 1H; 7.10–8.00 ppm, m, 7H. |
| 4 | 2,4-dichlorophenyl | $-CH_3$ | $-C_3H_7$ | $-CH_3$ | 3-chloro-4-pyridyl | (CDCl₃)Base 0.8 ppm, t, 3H; 1.26–1.74 ppm, m, 5H; 2.15 ppm, s, 3H; 3.17–3.33 ppm, m, 2H; 5.51 ppm, q, 1H; 7.25–7.45 ppm, m, 4H; 8.44–8.58 ppm, m, 2H. |
| 5 | 2,4-dichlorophenyl | $-CH_3$ | $-C_3H_7$ | $-CH_3$ | 2-methyl-4-pyridyl | (CDCl₃)Base 0.82 ppm, t, 3H; 1.42–1.74 ppm, m, 5H; 2.16 ppm, s, 3H; 2.54 ppm, s, 3H; 2.98–3.15 ppm, m, 2H; 5.56 ppm, q, 1H; 7.04–7.45 ppm, m, 5H; 8.43 ppm, d, 1H. |

TABLE VII-continued $$\begin{array}{c} R_2 \\ | \\ R_1 \end{array} C=C \begin{array}{c} S \\ | \\ N \end{array} C \begin{array}{c} N \diagdown R_3 \\ | \\ CH-R_6 \\ | \\ R_5 \end{array}$$

| EXAMPLE | $R_1$ | $R_2$ | $R_3$ | $R_5$ | $R_6$ | NMR SPECTRUM (SOLVENT) |
|---|---|---|---|---|---|---|
| 6 | 2,4-diCl-C$_6$H$_3$ | —CH$_3$ | —C$_3$H$_7$ | —CH$_3$ | 3-CH$_3$-pyridin-4-yl | (CDCl$_3$)Base 0.79 ppm, t, 3H; 1.18–1.78 ppm, m, 5H; 2.14 ppm, s, 3H; 3.16–3.32 ppm, m, 2H; 3.90 ppm, s, 3H; 5.44 ppm, q, 1H; 7.16–7.45 ppm, m, 4H; 8.21–8.25 ppm, m, 2H. |
| 7 | 2,4-diCl-C$_6$H$_3$ | —CH$_3$ | —C$_3$H$_7$ | —C$_2$H$_5$ | pyridin-4-yl | (CDCl$_3$)Base 0.80 ppm, t, 3H; 1.04 ppm, t, 3H;1.48–1.57 ppm, m, 1H; 1.92–2.17 ppm, m, 6H 2.95–3.11 ppm, m, 2H; 5.40 ppm, t, 1H; 7.27–7.48 ppm, m, 5H; 8.55 ppm, d, 2H. |
| 8 | 2,4-diCl-C$_6$H$_3$ | —CH$_3$ | —C$_3$H$_7$ | isopropyl | pyridin-4-yl | (CDCl$_3$)Base 0.81 ppm, t, 3H; 0.88 ppm, d, 3H; 1.04–1.47 ppm, m, 3H; 2.16 ppm, s, 3H; 2.44–2.75 ppm, m, 1H; 2.98–3.17 ppm, m, 2H; 5.04 ppm, d, 1H; 7.32–7.49 ppm, m, 5H; 8.56, d, 2H. |
| 9 | 2,4-diCl-C$_6$H$_3$ | —CH$_3$ | —C$_3$H$_7$ | cyclopropyl | 4-OCH$_3$-C$_6$H$_4$ | (CDCl$_3$)Base 0.3–1.0 ppm, m, 7H; 1.40 ppm, m, 1H; 1.70 ppm, m, 2H; 2.15 ppm, s, 3H; 3.15 ppm, m, 2H; 3.80 ppm, s, 3H; 4.60 ppm, d, 1H; 7.0–7.50, m, 7H. |
| 10 | 2,4-diCl-C$_6$H$_3$ | —CH$_3$ | —C$_3$H$_7$ | cyclopropyl | 4-tBu-C$_6$H$_4$ | (CDCl$_3$)Base 0.4–1.0 ppm, m 7H; 1.30 ppm, s, 9H; 1.40 ppm, m, 1H; 1.75 ppm, m, 2H 2.15 ppm, s, 3H; 3.15 ppm, m, 2H; 4.60 ppm, d, 1H; 7.2–7.45, m, 7H. |

TABLE VII-continued

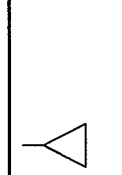

| EXAMPLE | R₁ | R₂ | R₃ | R₅ | R₆ | NMR SPECTRUM (SOLVENT) |
|---|---|---|---|---|---|---|
| 11 | 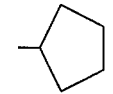 | —CH₃ | —C₃H₇ |  | 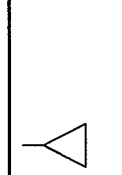 | (CDCl₃)Base 0.25–1.0 ppm, m, 7H; 1.2–1.9 ppm, m, 3H; 2.15 ppm, s, 3H; 3.25 ppm, m, 2H; 4.85 ppm, d, 1H; 6.9–7.5 ppm, m, 6H. |
| 12 | 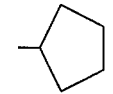 | —CH₃ | —C₃H₇ |  | 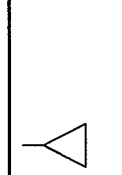 | (CDCl₃)Base 0.70 ppm, t, 3H; 0.97–1.62 ppm, m, 10H; 2.15 ppm, s, 3H; 2.70–3.24 ppm, m, 3H; 5.18 ppm, d, 1H; 7.21–7.47 ppm, m, 8H. |
| 13 | 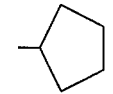 | —CH₃ | —C₃H₇ |  | 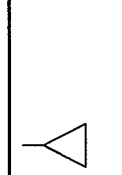 | (CDCl₃)Base 0.74 ppm, t, 3H; 0.90–1.90 ppm, m, 10H; 2.15 ppm, s, 3H; 2.29–3.20 ppm, m, 3H; 5.27 ppm, d, 1H; 7.23–7.48 ppm, m, 5H; 8.53 ppm, d, 2H. |
| 14 | 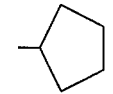 | —CH₃ | —C₃H₇ |  | 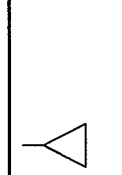 | (CDCl₃)Base 0.3–1.1 ppm, m, 7H; 1.4 ppm, m, 1H; 1.75 ppm, m, 2H; 2.2 ppm, s, 3H; 3.25 ppm, 2H; 4.75 ppm, d, 1H; 6.9–7.6 ppm, m, 7H. |
| 15 | 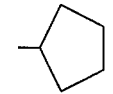 | —CH₃ | —C₃H₇ |  |  | (CDCl₃)Base 0.30–0.89 ppm, m, 7H; 1.26–1.76 ppm, m, 3H; 2.13 ppm, s, 3H; 3.30 ppm, t, 2H; 4.79 ppm, d, 1H; 7.22–7.45 ppm, m, 3H; 7.57 ppm, d, 1H; 8.47 ppm, d, 1H; 8.54 ppm, s, 1H. |

TABLE VII-continued $$R_2\underset{R_1}{\overset{S}{=}}\underset{N}{\overset{}{-}}\underset{}{\overset{R_3}{\underset{}{N-CH}\underset{R_5}{\overset{R_6}{}}}}$$

| EXAMPLE | R₁ | R₂ | R₃ | R₅ | R₆ | NMR SPECTRUM (SOLVENT) |
|---|---|---|---|---|---|---|
| 16 | 2,4-diCl-C₆H₃ | —CH₃ | —C₃H₇ | cyclopropyl | 2,4-(OCH₃)₂-C₆H₃ | (CDCl₃)Base 0.35–1.0 ppm, m, 7H; 1.1–1.8 ppm, m, 3H; 2.1 ppm, s, 3H; 3.25 ppm, m, 2H; 3.7 ppm, s, 3H; 3.8 ppm, s, 3H; 4.55 ppm, d, 1H; 6.45 ppm, s, 1H; 7.1–7.60 ppm, m, 5H. |
| 17 | 2,4-diCl-C₆H₃ | —CH₃ | —C₃H₇ | CH(C₂H₅)- isobutyl | 4-Cl-C₆H₄ | (CDCl₃)Base 0.6–1.8 ppm, m, 14H; 2.15 ppm, s, 3H; 3.05 ppm, m, 2H; 5.05, d, 1H; 7.1–7.5 ppm, m, 7H. |
| 18 | 2,4-diCl-C₆H₃ | —CH₃ | —C₃H₇ | cyclopropyl | 2-pyridyl | (CDCl₃)Base 0.35–0.92 ppm, m, 4H; 0.85 ppm, t, 3H; 1.56–1.81 ppm, m, 3H; 2.12 ppm, s, 3H; 3.29–3.54 ppm, m, 2H; 4.68 ppm d, 1H; 7.10–7.68 ppm, m, 6H; 8.58 ppm, d, 1H. |
| 19 | 2,4-diCl-C₆H₃ | —CH₃ | —C₃H₇ | phenyl | 4-pyridyl | (CDCl₃)Base 0.62 ppm, t, 3H; 0.81–1.67 ppm, m, 2H; 2.19 ppm, s, 3H; 3.26 ppm, m, 2H; 6.75 ppm, s, 1H; 7.13–7.43 ppm, m, 10H; 8.56 ppm, d, 2H. |
| 20 | 2,4-diCl-C₆H₃ | —CH₃ | —CH₂-cyclopropyl | —CH₃ | 4-pyridyl | (CDCl₃)Base 0.00–0.20 ppm, m, 2H; 0.42–0.52 ppm, m, 2H; 1.03–1.10 ppm, m, 1H; 1.67 ppm, d, 3H; 3.10 ppm, dd, 2H; 5.54 ppm, q, 1H; 7.23–7.34 ppm, m, 4H; 7.45 ppm, d, 1H; 8.55 ppm, d, 1H. |

TABLE VII-continued $$R_2 \underset{R_1}{\overset{S}{=}} \underset{N}{\overset{R_3}{\underset{CH}{\overset{R_6}{\underset{R_5}{}}}}}$$

| EXAMPLE | R₁ | R₂ | R₃ | R₅ | R₆ | NMR SPECTRUM (SOLVENT) |
|---|---|---|---|---|---|---|
| 21 | 6-methyl-2-naphthyl | —CH₃ | —C₃H₇ | —CH₃ | 4-pyridyl | (CDCl₃)Base 0.87 ppm, t, 3H; 1.55–1.75 ppm, m, 3H+2H; 2.51 ppm, s, 3H; 3.05–3.20 ppm, m, 2H; 5.71 ppm, q, 1H; 7.20–7.50 ppm, m, 4H; 7.70–7.90 ppm, m, 4H; 8.03 ppm, s, 1H; 8.59 ppm, d, 2H. |
| 22 | 2-OCH₃-4-Cl-phenyl | —CH₃ | —C₃H₇ | —CH₃ | 4-pyridyl | (DMSO-d₆)Oxalate salt 0.89 ppm, t, 3H; 1.50–1.70 ppm, m, 2H+3H; 2.13 ppm, s, 3H; 3.20–3.35 ppm, m, 2H; 3.86 ppm, s, 3H; 5.50 ppm, q, 1H; 7.10 ppm, dd, 1H; 7.21 ppm, d, 1H; 7.33 ppm, d, 1H; 7.45 ppm, d, 2H; 8.63 ppm, d, 2H. |
| 23 | 2,4-dimethyl-phenyl | —CH₃ | —C₃H₇ | —CH₃ | 4-pyridyl | (CDCl₃)Base 0.83 ppm, t, 3H; 1.50–1.70 ppm, m, 3H+2H; 2.17 ppm, s, 3H; 2.19 ppm, s, 3H; 2.33 ppm, s, 3H; 2.90–3.05 ppm, m, 2H; 5.50–5.70 ppm, q, 1H; 7.00–7.15 ppm, m, 2H; 7.17 ppm, d, 1H; 7.25 ppm, d, 2H; 8.55 ppm, d, 2H. |
| 24 | 2-methyl-4-Cl-phenyl | —CH₃ | —C₃H₇ | —CH₃ | 4-pyridyl | (CDCl₃)Base 0.84 ppm, t, 3H; 1.5–1.7 ppm, m, 3H+2H; 2.15 ppm, s, 3H; 2.19 ppm, s, 3H; 3.0–3.3 ppm, m, 2H; 5.60 ppm, q, 1H; 7.1–7.4 ppm, m, 5H; 8.55 ppm, d, 2H. |
| 25 | 2,4-dichloro-phenyl | H | —C₃H₇ | —CH₃ | 4-pyridyl | (CDCl₃)Base 0.87 ppm, t, 3H; 1.59–1.71 ppm, m, 3H+2H; 3.10–3.23 ppm, m, 2H; 5.65 ppm, q, 1H; 7.14 ppm, s, 1H; 7.23–7.30 ppm, m, 3H; 7.43 ppm, d, 1H; 7.88 ppm, d, 1H; 8.57 ppm, d, 2H. |

TABLE VII-continued $$R_2 \underset{R_1}{\overset{S}{=}} \underset{N}{\overset{R_3}{\underset{}{\bigg\rangle}}} N \underset{}{\overset{R_3}{\underset{}{\bigg\langle}}} \underset{R_5}{\overset{R_6}{\underset{}{CH}}}$$

| EXAMPLE | R₁ | R₂ | R₃ | R₅ | R₆ | NMR SPECTRUM (SOLVENT) |
|---|---|---|---|---|---|---|
| 26 | 3-Cl-4-CH₃-phenyl | —CH₃ | —C₃H₇ | —CH₃ | 4-pyridyl | (CDCl₃)Base 0.83 ppm, t, 3H; 1.50–1.70 ppm, m, 3H+2H; 2.17 ppm, s, 3H; 2.35 ppm, s, 3H; 3.0–3.3 ppm, m, 2H; 5.7 ppm, q, 1H; 7.09 ppm, d, 1H; 7.35–7.40 ppm, m, 4H; 8.55 ppm, d, 2H. |
| 27 | 3-Cl-4-OCH₃-phenyl | —CH₃ | —C₃H₇ | —CH₃ | 4-pyridyl | (CDCl₃)Base 0.83 ppm, t, 3H; 1.50–1.76 ppm, m, 3H+2H; 2.17 ppm, s, 3H; 3.0–3.1 ppm, m, 2H; 3.81 ppm, s, 3H; 5.68 ppm, q, 1H; 6.64 ppm, dd, 1H; 6.98 ppm, d, 1H; 7.20–7.30 ppm, m, 3H; 8.57 ppm, m, 2H. |
| 28 | 4-CH₃-phenyl | —CH₃ | —C₃H₇ | —CH₃ | 4-pyridyl | (CDCl₃)Base 0.91 ppm, t, 3H; 1.61–1.67 ppm, m, 3H+2H; 2.37 ppm, s, 3H; 2.42 ppm, s, 3H; 3.03–3.12 ppm, m, 2H; 5.66 ppm, q, 1H; 7.20 ppm, d, 2H; 7.28 ppm, d, 2H; 7.50 ppm, d, 2H; 7.56 ppm, d, 2H. |
| 29 | 2,4-di-OCH₃-phenyl | —CH₃ | —C₃H₇ | —CH₃ | 4-pyridyl | (CDCl₃)Base 0.83 ppm, t, 3H; 1.58–1.75 ppm, m, 3H+2H; 2.15 ppm, s, 3H; 3.23–3.45 ppm, m, 2H; 3.90 ppm, s, 3H; 3.99 ppm, s, 3H; 5.55 ppm, q, 1H; 6.52 ppm, 2s, 2H; 7.27 ppm, 2H; 7.57 ppm, s, 1H; 8.56 ppm, d, 2H. |
| 30 | 4-OCH₃-phenyl | —CH₃ | —C₃H₇ | —CH₃ | 4-pyridyl | (CDCl₃)Base 0.85 ppm, t, 3H; 1.50–1.60 ppm, m, 5H; 2.41 ppm, s, 3H; 3.08 ppm, m, 2H; 3.83 ppm, s, 3H; 5.67 ppm, q, 1H; 7.25 ppm, m, 4H; 7.90 ppm, m, 4H. |

TABLE VII-continued $$R_2 \overset{S}{\underset{R_1}{=}} \overset{N-R_3}{\underset{N}{\diagdown}} \overset{R_6}{\underset{R_5}{CH}}$$

| EXAMPLE | R₁ | R₂ | R₃ | R₅ | R₆ | NMR SPECTRUM (SOLVENT) |
|---|---|---|---|---|---|---|
| 31 | 4-Cl-C₆H₄ | —CH₃ | —C₃H₇ | —CH₃ | 4-pyridyl | (CDCl₃)Base 0.85 ppm, t, 3H; 1.56–1.66 ppm, m, 3H+2H; 2.41 ppm, s, 3H; 3.04–3.17 ppm, m, 2H; 5.62 ppm, q, 1H; 7.27–7.38 ppm, m, 4H; 7.55 ppm, d, 2H; 8.56 ppm, d, 2H. |
| 32 | 2,4-diCl-C₆H₃ | —CH₃ | —C₃H₇ | —CH₃ | phenyl | (CDCl₃)Base 0.77 ppm, t, 3H; 1.22–1.66 ppm, m, 5H; 2.16 ppm, s, 3H; 2.90–3.14 ppm, m, 2H; 5.57 ppm, q, 1H; 7.20–7.47 ppm, m, 8H. |
| 33 | 2,4-diCl-C₆H₃ | —CH₃ | —C₃H₇ | —CH₃ | 4-pyridyl | (DMSO-d₆)Oxalate salt 0.92 ppm, t, 3H; 1.72 ppm, m, 2H; 1.74 ppm, d, 3H; 2.16 ppm, s, 3H; 3.22 ppm, t, 2H; 5.68 ppm, q, 1H; 7.23 ppm, m, 2H; 7.41 ppm, s, 1H; 7.77 ppm, d, 2H; 8.79 ppm, d, 2H. |
| 34 | 2,4,6-triMe-C₆H₂ | H | —C₃H₇ | —CH₃ | 4-pyridyl | (DMSO-d₆)Fumarate salt 0.83 ppm, t, 3H; 1.63 ppm, m, 5H; 1.99 ppm, s, 6H; 2.24 ppm, s, 3H; 3.25 ppm, t, 2H; 5.36 ppm, q, 1H; 6.51 ppm, s, 1H; 6.64 ppm, s, 2H; (fumaric acid); 6.84 ppm, s, 2H; 7.30 ppm, d, 2H; 8.52 ppm, d, 2H. |
| 35 | 2,4,6-triMe-C₆H₂ | H | —C₃H₇ | —CH₃ | 2-pyridyl | (DMSO-d₆)Base 1.0 ppm, t, 3H; 1.6 ppm, m, 2H; 1.8 ppm, d, 3H; 2.2 ppm, s, 6H; 2.4 ppm, s, 3H; 3.4 ppm, m, 2H; 5.5 ppm, q, 1H; 6.6 ppm, s, 1H; 7.0 ppm, s, 2H; 7.5 ppm, m, 1H; 7.9 ppm, m, 1H; 8.65 ppm, m, 2H. |

TABLE VII-continued $$\underset{R_2}{\overset{R_1}{\diagdown}}C=C\overset{S}{\underset{N}{\diagdown}}\overset{R_3}{\underset{\overset{|}{CH}-R_5}{\diagdown}}\overset{R_6}{\underset{}{}}$$

| EXAMPLE | $R_1$ | $R_2$ | $R_3$ | $R_5$ | $R_6$ | NMR SPECTRUM (SOLVENT) |
|---|---|---|---|---|---|---|
| 36 | 2,4-dichlorophenyl | —CH$_3$ | —CH$_2$—CH(CH$_3$)$_2$ | —CH$_3$ | 4-pyridyl | (DMSO-d$_6$)Oxalate salt 0.84 ppm, m, 6H; 1.64 ppm, d, 3H; 2.0 ppm, m, 1H; 2.11 ppm, s, 3H; 3.12 ppm, t, 2H; 5.29 ppm, q, 1H; 7.42 ppm, m, 4H; 7.68 ppm, s, 1H; 8.56 ppm, m, 2H. |
| 37 | 2,3,5-trimethylphenyl | H | —CH$_3$ | —CH$_3$ | 2-methyl-6-pyridyl | (DMSO-d$_6$)Base 1.50 ppm, d, 3H; 2.1 ppm, s, 6H; 2.3 ppm, s, 3H; 2.43 ppm, s, 3H; 2.7 ppm, s, 3H; 5.7 ppm, q, 1H; 6.55 ppm, s, 1H; 6.9 ppm, s, 2H; 7.3 ppm, m, 1H; 7.85 ppm, d, 1H; 8.42 ppm, d, 1H. |
| 38 | 2,3,5-trimethylphenyl | H | —C$_2$H$_5$ | —CH$_3$ | 4-pyridyl | (DMSO-d$_6$)Base 1.20 ppm, t, 3H; 1.75 ppm, d, 3H; 2.15 ppm, s, 6H; 2.3 ppm, s, 3H; 3.5 ppm, m, 2H; 5.5 ppm, q, 2H; 6.65 ppm, s, 1H; 7.0 ppm, s, 2H; 7.4 ppm, m, 2H; 8.6 ppm, m, 2H. |
| 39 | 2,3,5-trimethylphenyl | H | cyclopropyl | —CH$_3$ | 4-pyridyl | (DMSO-d$_6$)Hydrochloride salt 1.10 ppm, m, 4H; 1.90 ppm, d, 3H; 2.00 ppm, s, 6H; 2.3 ppm, s, 3H; 3.0 ppm, m, 1H; 5.6 ppm, q, 1H; 6.90 ppm, s, 2H; 7.0 ppm, s, 2H; 8.2 ppm, m, 1H; 8.6 ppm, m, 1H; 8.9 ppm, m, 2H. |
| 40 | 1-naphthyl | —CH$_3$ | —C$_3$H$_7$ | | 4-pyridyl | (CDCl$_3$)Base 0.88 ppm, t, 3H; 1.50–1.75 ppm, m, 5H; 2.19 ppm, s, 3H; 3.10–3.25 ppm, m, 2H; 5.87 ppm, q, 1H; 7.25–7.55 ppm, m, 6H; 7.80–7.90 ppm, m, 3H; 8.59 ppm, d, 2H. |

TABLE VII-continued

| EXAMPLE | R₁ | R₂ | R₃ | R₅ | R₆ | NMR SPECTRUM (SOLVENT) |
|---|---|---|---|---|---|---|
| 41 | 2,4-Cl₂-C₆H₃ | —CH₃ | —CH₂-cyclopropyl | —CH₃ | phenyl | (CDCl₃)Base 0.31–1.22 ppm, m, 5H; 1.67 ppm, d, 3H; 2.16 ppm, s, 3H; 2.84–3.28 ppm, m, 2H; 5.47 ppm, q, 1H; 7.21–7.49 ppm, m, 8H. |
| 42 | 2,4-Cl₂-C₆H₃ | —CH₃ | —C₃H₇ | cyclopropyl | imidazolyl (NH) | (CDCl₃)Base 0.33–0.93 ppm, m, 7H; 1.40–1.83 ppm, m, 3H; 2.16 ppm, s, 3H; 3.22–3.37 ppm, m, 2H; 4.33 ppm, d, 1H; 7.27–7.31 ppm, m, 4H; 7.50 ppm, s, 1H. |
| 43 | 2,4-Cl₂-C₆H₃ | —CH₃ | —C₃H₇ | —CH₃ | imidazolyl (NH) | (CDCl₃)Base 0.84 ppm, t, 3H; 1.44–1.81 ppm, m, 5H; 2.16 ppm, s, 3H; 3.15 ppm, t, 2H; 5.40 ppm, q, 1H; 7.21–7.38 ppm, m, 4H; 7.50 ppm, s, 1H. |
| 44 | 2,4-Cl₂-C₆H₃ | —CH₃ | —C₃H₇ | cyclopropyl | N-benzyl imidazolyl | (CDCl₃)Base 0.31–0.92 ppm, m, 7H; 1.41–1.83 ppm, m, 3H; 2.10 ppm, s, 3H; 3.22–3.10 ppm, m, 2H; 4.50 ppm, d, 1H; 5.04 ppm, s, 2H; 6.87 ppm, s, 1H; 7.10–7.46 ppm, m, 9H. |
| 45 | 2,4-Cl₂-C₆H₃ | —CH₃ | —C₃H₇ | cyclopropyl | N-methyl imidazolyl | (CDCl₃)Base 0.33–0.95 ppm, m, 7H; 1.39 ppm, m, 3H; 2.11 ppm, s, 3H; 3.10–3.57 ppm, m, 2H; 3.62 ppm, s, 3H; 4.46 ppm, d, 1H; 6.85 ppm, s, 1H; 7.19–7.44 ppm, m, 5H. |

TABLE VII-continued

| EXAMPLE | R$_1$ | R$_2$ | R$_3$ | R$_5$ | R$_6$ | NMR SPECTRUM (SOLVENT) |
|---|---|---|---|---|---|---|
| 46 | 2,4-dichlorophenyl | —Br | —C$_3$H$_7$ | —CH$_3$ | 4-pyridyl | (CDCl$_3$)Base 0.84 ppm, t, 3H; 1.54–1.66 ppm, m, 5H; 3.03–3.13 ppm, m, 2H; 5.61 ppm, q, 1H; 7.24–7.40 ppm, m, 4H; 7.47 ppm, d, 1H; 8.57 ppm, d, 2H. |
| 47 | 2,4-dichlorophenyl | —CH$_3$ | —C$_3$H$_7$ | cyclopropyl | cyclopropyl | (CDCl$_3$)Base 0.30–0.72 ppm, m, 8H; 0.89–1.26 ppm, m, 5H; 1.84 ppm, m, 2H; 2.12 ppm, s, 3H; 3.11 ppm, t, 1H; 3.38 ppm, t, 2H; 7.28–7.45 ppm, m, 3H. |
| 48 | 2,4-dichlorophenyl | —CH$_3$ | —C$_3$H$_7$ | cyclopropyl | cyclopentyl | (CDCl$_3$)Base 0.27–0.78 ppm, m, 4H; 0.93 ppm, t, 3H; 1.29–2.01 ppm, m, 12H; 2.11 ppm, s, 3H; 3.00–3.47 ppm, m, 3H; 7.18–7.43 ppm, m, 3H. |
| 49 | 2,4-dichlorophenyl | —CHO | —C$_3$H$_7$ | —CH$_3$ | 4-pyridyl | (CDCl$_3$)Base 0.87 ppm, t, 3H; 1.54–1.72 ppm, m, 5H; 3.11–3.26 ppm, m, 2H; 5.82 ppm, s, 1H; 7.24 ppm, d, 2H; 7.32–7.42 ppm, m, 2H; 7.52 ppm, dd, 1H; 8.60 ppm, d, 2H; 9.42 ppm, s, 1H. |
| 50 | 2,4-dichlorophenyl | —CH$_2$OH | —C$_3$H$_7$ | —CH$_3$ | 4-pyridyl | (CDCl$_3$)Base 0.84 ppm, t, 3H; 1.55–1.75 ppm, m, 5H; 2.26 ppm, s, 1H; 3.05–3.16 ppm, m, 2H; 4.33 ppm, s, 2H; 5.68 ppm, q, 1H; 7.24–7.34 ppm, m, 4H; 7.45 ppm, s, 1H; 8.52 ppm, d, 2H. |

TABLE VII-continued structure: R2, R1 on C=C with S, connected to C=N-CH(R5)(R6) with N-R3

| EXAMPLE | R₁ | R₂ | R₃ | R₅ | R₆ | NMR SPECTRUM (SOLVENT) |
|---|---|---|---|---|---|---|
| 51 | 2,4-dichlorophenyl | —CH₃ | —CH₂—CH=CH₂ | —CH₃ | 4-pyridyl | (CDCl₃)Base 1.52–1.56 ppm, d, 3H; 2.07 ppm, s, 3H; 3.69–3.73 ppm, m, 2H; 5.05–5.17 ppm, m, 2H; 5.61–5.70 ppm, m, 2H; 7.14–7.37 ppm, m, 5H; 8.46–8.49 ppm, m, 2H. |
| 52 | 2-hydroxy-5-chlorophenyl | —CH₃ | —C₃H₇ | —CH₃ | 4-pyridyl | (CDCl₃)Base 0.88 ppm, t, 3H; 1.50–1.70 ppm, m, 5H; 2.46 ppm, s, 3H; 3.00–3.25 ppm, m, 2H; 5.23 ppm, q, 1H; 6.83 ppm, dd, 1H; 6.94 ppm, d, 1H; 7.21 ppm, d, 2H; 7.33 ppm, d, 1H; 8.58 ppm, d, 2H. |
| 53 | 2-chloro-4-hydroxyphenyl | —CH₃ | —C₃H₇ | —CH₃ | 4-pyridyl | (CDCl₃)Base 0.87 ppm, t, 3H; 1.65–1.68 ppm, m, 5H; 2.14 ppm, s, 3H; 3.16–3.18 ppm, m, 2H; 5.50 ppm, q, 1H; 6.60 ppm, dd, 1H; 6.75 ppm, s, 1H; 7.07 ppm, d, 2H; 7.30 ppm, d, 1H; 8.54 ppm, dd, 2H. |
| 54 | 2,4-dichlorophenyl | —CH₃ | —C₃H₇ | cyclopropyl | 3-pyridyl | (CDCl₃)Base 0.42 ppm, m, 1H; 0.65 ppm, m, 2H; 0.82 ppm, m, 4H; 1.35 ppm, m, 1H; 1.68 ppm, m, 2H; 2.11 ppm, s, 3H; 3.22 ppm, m, 2H; 4.74 ppm, d, 1H; 7.08–7.24 ppm, m, 3H; 7.73 ppm, d, 1H; 8.45 ppm, d, 1H; 8.76 ppm, d, 1H. |
| 55 | 2-chloro-4-methoxyphenyl | —CH₃ | —C₃H₇ | cyclopropyl | cyclopropyl | (CDCl₃)Base 0.3–0.7 ppm, m, 8H; 0.8–1.2 ppm, m, 5H; 2.11 ppm, s, 3H; 3.13 ppm, t, 1H; 3.36 ppm, m, 2H; 3.79 ppm, s, 3H; 6.7–7.0 ppm, m, 2H; 7.28 ppm, d, 1H. |

TABLE VII-continued $$\underset{R_2}{\overset{R_1}{>}}=\underset{S}{\overset{}{\underset{}{\bigvee}}}\underset{N}{\overset{R_3}{\underset{}{\bigvee}}}\underset{R_5}{\overset{CH-R_6}{}}$$

| EXAMPLE | R₁ | R₂ | R₃ | R₅ | R₆ | NMR SPECTRUM (SOLVENT) |
|---------|-----|-----|-----|-----|-----|------------------------|
| 56 | 4-CH₃-3-Cl-phenyl | —CH₃ | —C₃H₇ | cyclopropyl | cyclopropyl | (CDCl₃)Base 0.3–0.7 ppm, m, 8H; 0.9–1.25 ppm, m, 5H; 1.7–2.0 ppm, m, 2H; 2.12 ppm, s, 3H; 2.33 ppm, s, 3H; 3.14 ppm, t, 1H; 3.37 ppm, m, 2H; 7.0–7.3 ppm, m, 3H. |
| 57 | 2,4-dichlorophenyl | —CH₃ | —C₃H₇ | cyclobutyl | phenyl | (CDCl₃)Base 0.75 ppm, m, 3H; 1.2–2.1 ppm, m, 8H; 2.06 ppm, s, 3H; 2.8–3.2 ppm, m, 3H; 5.53 ppm, d, 1H; 7.2–7.5 ppm, m, 8H. |
| 58 | 2-Cl-4-OCH₃-phenyl | —CH₃ | —C₃H₇ | cyclobutyl | phenyl | (CDCl₃)Base 0.75 ppm, m, 3H; 1.3–2.1 ppm, m, 8H; 2.16 ppm, s, 3H; 2.8–3.2 ppm, m, 3H; 3.80 ppm, s, 3H; 5.65 ppm, d, 1H; 6.8–7.4 ppm, m, 8H. |
| 59 | 2,4-dichlorophenyl | —CH₃ | —C₃H₇ | cyclopropyl | 2,4-dichlorophenyl | (CDCl₃)Base 0.3–1.0 ppm, m, 7H; 1.2–1.8 ppm, m, 3H; 2.13 ppm, s, 3H; 3.25 ppm, m, 2H; 4.82 ppm, d, 1H; 7.1–7.7 ppm, m, 6H. |
| 60 | 2,4-dichlorophenyl | —CH₃ | —C₃H₇ | cyclopropyl | 4-bromophenyl | (CDCl₃)Base 0.3–1.0 ppm, m, 7H; 1.2–1.8 ppm, m, 3H; 2.15 ppm, s, 3H; 3.20 ppm, m, 2H; 4.67 ppm, d, 1H; 7.1–7.7 ppm, m, 7H. |

TABLE VII-continued $$R_2 \diagdown_{R_1} C = C \diagdown_{S}^{N} C \diagdown_{N}^{R_3} CH \diagdown_{R_5}^{R_6}$$

| EXAMPLE | R₁ | R₂ | R₃ | R₅ | R₆ | NMR SPECTRUM (SOLVENT) |
|---|---|---|---|---|---|---|
| 61 | 2,4-dichlorophenyl | —CH₃ | —C₃H₇ | cyclopropyl | 3,4-dimethoxyphenyl | (CDCl₃)Base 0.35–1.0 ppm, m, 7H; 1.2–1.9 ppm, m, 3H; 2.18 ppm, s, 3H; 3.2 ppm, m, 2H; 3.85 ppm, s, 3H; 3.90 ppm, s, 3H; 4.66 ppm, d, 1H; 6.75–7.5 ppm, m, 6H. |
| 62 | 2-methoxy-4-chlorophenyl | —CH₃ | —C₃H₇ | cyclopropyl | phenyl | (CDCl₃)Base 0.4–1.1 ppm, m, 7H; 1.3–1.9 ppm, m, 3H; 2.25 ppm, s, 3H; 3.36 ppm, m, 2H; 3.88 ppm, s, 3H; 4.85 ppm, d, 1H; 6.95–7.8 ppm, m, 8H. |
| 63 | 2-chloro-4-methoxyphenyl | —CH₃ | —C₃H₇ | cyclopropyl | phenyl | (CDCl₃)Base 0.54 ppm, m, 1H; 0.7–1 ppm, m, 6H; 1.5 ppm, m, 1H; 1.84 ppm, m, 2H; 2.25 ppm, s, 3H; 3.31 ppm, q, 2H; 3.82 ppm, s, 3H; 4.84 ppm, d, 1H; 6.90 ppm, m, 1H; 7.07 ppm, m, 1H; 7.37 ppm, m, 4H; 7.60 ppm, m, 2H. |
| 64 | 2,4-dichlorophenyl | —CH₃ | —C₃H₇ | cyclopropyl | 4-chlorophenyl | (CDCl₃)Base 0.3–1.0 ppm, m, 7H; 1.1–1.8 ppm, m, 3H; 2.13 ppm, s, 3H; 3.15 ppm, m, 2H; 4.70 ppm, d, 1H; 7–7.5 ppm, m, 7H. |
| 65 | 2,4-dichlorophenyl | —CH₃ | —C₃H₇ | cyclopropyl | 3-methylphenyl | (CDCl₃)Base 0.3–0.95 ppm, m, 7H; 1.1–1.9 ppm, m, 3H; 2.13 ppm, s, 3H; 2.32 ppm, s, 3H; 3.15 ppm, m, 2H; 4.62 ppm, d, 1H; 6.85–7.5 ppm, m, 7H. |

TABLE VII-continued

Structure: R₂(R₁)C=C(S-)(C(=N-CH(R₅)(R₆))-N(R₃))

| EXAMPLE | R₁ | R₂ | R₃ | R₅ | R₆ | NMR SPECTRUM (SOLVENT) |
|---|---|---|---|---|---|---|
| 66 | 2-CH₃-4-Cl-phenyl | —CH₃ | —C₃H₇ | cyclopropyl | phenyl | (CDCl₃)Base 0.3–0.95 ppm, m, 7H; 1.15–1.8 ppm, m, 3H; 2.16 ppm, s, 3H; 2.27 ppm, s, 3H; 3.15 ppm, m, 2H; 4.68 ppm, d, 1H; 7.0–7.5 ppm, m, 8H. |
| 67 | 2-Cl-4-CH₃-phenyl | —CH₃ | —C₃H₇ | cyclopropyl | phenyl | (CDCl₃)Base 0.3–1.0 ppm, m, 7H; 1.1–1.8 ppm, m, 3H; 2.18 ppm, s, 3H; 2.34 ppm, s, 3H; 3.1 ppm, m, 2H; 4.73 ppm, d, 1H; 6.9–7.5 ppm, m, 8H. |
| 68 | 2,4-di-Cl-phenyl | —CH₃ | —C₃H₇ | —CH₃ | 2-Cl-pyridin-4-yl | (CDCl₃)Base 0.86 ppm, m, 3H; 1.5–1.7 ppm, m, 5H; 2.16 ppm, s, 3H; 3.0–3.2 ppm, m, 2H; 5.63 ppm, q, 1H; 7.1–7.4 ppm, m, 5H; 8.31 ppm, d, 1H. |
| 69 | 2,4-di-Cl-phenyl | —CH₃ | —C₃H₇ | cyclopropyl | 2-CH₃-pyridin-4-yl | (CDCl₃)Base 0.5–0.9 ppm, m, 7H; 1.3–1.4 ppm, m, 1H; 1.6–1.8 ppm, m, 2H; 2.16 ppm, s, 3H; 2.54 ppm, s, 3H; 3.1–3.3 ppm, m, 2H, 4.68 ppm, d, 1H; 7.20 ppm, d 1H; 7.43 ppm, s, 1H; 8.41 ppm, d, 1H. |
| 70 | 2,4-di-Cl-phenyl | —CH₃ | —C₃H₇ | —CH₃ | cyclopropyl | (CDCl₃)Base 0.3–0.5 ppm, m, 4H; 0.95 ppm, m, 4H; 1.29 ppm, d, 3H; 1.79 ppm, m, 2H; 2.13 ppm, s, 3H; 3.27–3.52 ppm, m, 3H; 7.2–7.5 ppm, m, 3H. |

TABLE VII-continued

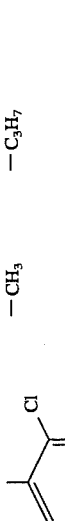

| EXAMPLE | $R_1$ | $R_2$ | $R_3$ | $R_5$ | $R_6$ | NMR SPECTRUM (SOLVENT) |
|---|---|---|---|---|---|---|
| 71 | 2,4-di-Cl-phenyl | —CH$_3$ | —C$_3$H$_7$ | cyclopropyl | cyclobutyl | (CDCl$_3$)Base 0.2–1.0 ppm, m, 8H; 1.5–2.1 ppm, m, 8H; 2.16 ppm, s, 3H; 2.5–2.8 ppm, m, 1H; 3.1–3.4 ppm, m, 3H; 7.1–7.4 ppm, m, 3H. |
| 72 | 2,4-di-Cl-phenyl | —CH$_3$ | —C$_3$H$_7$ | —CH$_2$—CH$_2$—CH=CH$_2$ | phenyl | (CDCl$_3$)Base 0.73 ppm, m, 3H; 1.45 ppm, m, 2H; 2.15 ppm, m, 7H; 3.03 ppm, m, 2H; 4.93–5.10 ppm, m, 2H; 5.42 ppm, t, 1H; 5.80 ppm, m, 1H; 7.21–7.45 ppm, m, 8H. |
| 73 | 2,4-di-Cl-phenyl | —CH$_3$ | —C$_3$H$_7$ | —CH$_2$-cyclopropyl | phenyl | (CDCl$_3$)Base 0.15 ppm, m, 2H; 0.40 ppm, m, 2H; 0.71 ppm, m, 4H; 1.45 ppm, m, 2H; 1.92 ppm, m, 2H; 2.12 ppm, s, 3H; 3.06 ppm, m, 2H; 5.33 ppm, t, 1H; 7.15–7.43 ppm, m, 8H. |
| 74 | 2,4-di-Cl-phenyl | —CH$_3$ | —C$_3$H$_7$ | —C(CH$_3$)-cyclopropyl | —C(CH$_3$)-cyclopropyl | (CDCl$_3$)Base 0.3–0.5 ppm, m, 4H; 0.5–0.7 ppm, m, 4H; 0.89 ppm, m, 3H; 1.21 ppm, s, 6H; 2.7–2.9 ppm, m, 2H; 2.13 ppm, s, 3H; 3.3–3.5 ppm, m, 3H; 7.2–7.4 ppm, m, 3H. |
| 75 | 2,4-di-Cl-phenyl | —CH$_3$ | —C$_3$H$_7$ | —CH$_2$-phenyl | cyclopropyl | (CDCl$_3$)Base 0.1–0.15 ppm, m, 2H; 0.25–0.6 ppm, m, 2H; 0.9 ppm, m, 3H; 1.1–1.3 ppm, m, 1H; 1.7–1.85 ppm, m, 2H; 2.14 ppm, s, 3H; 2.9–3.4 ppm, m, 5H; 7.1–7.6 ppm, m, 8H. |

TABLE VII-continued $$R_2 \underset{R_1}{\overset{S}{\diagdown}} \underset{N}{\overset{}{=}} \underset{}{\overset{R_3}{\diagup}} N \underset{}{\overset{R_6}{\diagdown}} CH \underset{R_5}{\overset{}{\diagup}}$$

| EXAMPLE | R₁ | R₂ | R₃ | R₅ | R₆ | NMR SPECTRUM (SOLVENT) |
|---|---|---|---|---|---|---|
| 76 | 4-OCH₃-phenyl | —CH₃ | —C₃H₇ | cyclopropyl | cyclopropyl | (CDCl₃)Base 0.4–0.5 ppm, m, 8H; 0.9–1.2 ppm, m, 5H; 1.7–1.9 ppm, m, 2H; 2.37 ppm, s, 3H; 3.04 ppm, t, 1H; 3.40 ppm, m, 2H; 3.82 ppm, s, 3H; 6.91 ppm, d, 2H; 7.54 ppm, d, 2H. |
| 77 | 4-Cl-phenyl | —CH₃ | —C₃H₇ | cyclopropyl | cyclopropyl | (CDCl₃)Base 0.2–0.8 ppm, m, 8H; 0.98 ppm, t, 3H; 1 ppm, m, 2H; 1.85 ppm, q, 2H; 2.37 ppm, s, 3H; 3.0 ppm, t, 1H; 2.4 ppm, m, 2H; m, 7.24–7.6 ppm, m, 4H. |
| 78 | 2,4-diCl-phenyl | —CH₃ | —C₃H₇ | H₃C—C(CH₃)₂— | phenyl | (CDCl₃)Base 0.71 ppm, t, 3H; 1.0 ppm, m, 1H; 1.18 ppm, s, 9H; 1.70 ppm, m, 1H; 2.17 ppm, s, 3H; 3.40 ppm, m, 2H; 5.28 ppm, s, 1H; 7.24–7.56 ppm, m, 8H. |
| 79 | 2,4-diCl-phenyl | —CH₃ | —C₃H₇ | cyclopropyl | —C(CH₃)(cyclopropyl) | (CDCl₃)Base 0.3–0.9 ppm, m, 9H; 0.95 ppm, t, 3H; 1.10 ppm, s, 3H; 1.80 ppm, m, 2H; 2.13 ppm, s, 3H; 3.5 ppm, m, 3H; 7.4 ppm, m, 3H. |
| 80 | 2,4-diCl-phenyl | —CH₃ | —C₃H₇ | cyclobutyl | cyclobutyl | (CDCl₃)Base 0.9 ppm, t, 3H; 1.9 ppm, m, 16H; 2.1 ppm, t, 2H; 2.13 ppm, s, 3H; 3.2 ppm, m, 2H; 4.0 ppm, t, 1H; 7.5 ppm, m, 3H. |

TABLE VII-continued

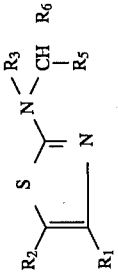

| EXAMPLE | R₁ | R₂ | R₃ | R₅ | R₆ | NMR SPECTRUM (SOLVENT) |
|---|---|---|---|---|---|---|
| 81 | 2,4-diCl-phenyl | —CH₃ | —C₃H₇ | —CH₂-cyclopropyl | cyclopropyl | (CDCl₃)Base 0.02–1.0 ppm, m, 11H; 1.3–2.1 ppm, m, 7H; 2.12 ppm, s, 3H; 3.1–3.4 ppm, m, 3H; 7.1–7.4 ppm, m, 3H. |
| 82 | 2,4-diCl-phenyl | H | —C₃H₇ | cyclopropyl | phenyl | (CDCl₃)Base 0.3–1 ppm, m, 7H; 1.2–1.9 ppm, m, 3H; 3.25 ppm, m, 2H; 4.73 ppm, d, 1H; 7–7.6 ppm, m, 8H; 7.95 ppm, m, 1H. |
| 83 | 2,4-diCl-phenyl | —CH₃ | phenyl | cyclopropyl | phenyl | (CDCl₃)Base 0.3–1.3 ppm, m, 5H; 2.04 ppm, s, 3H; 5.2 ppm, d, 1H; 7.0–7.5 ppm, m, 13H. |
| 84 | 2,4-diCl-phenyl | —CH₃ | phenyl | cyclopropyl | cyclopropyl | (CDCl₃)Base 0.3–0.9 ppm, m, 10H; 1.99 ppm, s, 3H; 3.6 ppm, t, 1H; 7.43 ppm, m, 8H. |
| 85 | 2,4-diBr-phenyl | —CH₃ | —C₃H₇ | cyclopropyl | cyclopropyl | (CDCl₃)Base 0.5–0.8 ppm, m, 8H; 1.05 ppm, t, 3H; 1.6–1.9 ppm, m, 4H; 2.06 ppm, s, 3H; 3.67 ppm, m, 3H; 7.2–7.8 ppm, m, 3H. |

TABLE VII-continued structure:
$R_2\text{-}R_1$ with $C=C$, S, $C(=N)\text{-}N(R_3)\text{-}CH(R_5)(R_6)$

| EXAMPLE | R₁ | R₂ | R₃ | R₅ | R₆ | NMR SPECTRUM (SOLVENT) |
|---|---|---|---|---|---|---|
| 86 | 2,4-dibromophenyl | —CH₃ | —C₃H₇ | cyclopropyl | phenyl | (CDCl₃)Hydrochloride 0.6–0.9 ppm, m, 7H; 1.1–1.8 ppm, m, 3H; 2.09 ppm, s, 3H; 3.6 ppm, m, 2H; 4.9 ppm, m, 1H; 7.6 ppm, m, 7H; 7.81 ppm, m, 1H. |
| 87 | 2,4-dichlorophenyl | —CH₃ | —C₃H₇ | cyclopropyl | 4-iodophenyl | (CDCl₃)Base 0.3–1 ppm, m, 7H; 1.2–1.9 ppm, m, 3H; 2.15 ppm, s, 3H; 3.2 ppm, m, 2H; 4.68 ppm, d, 1H; 7.15–7.8 ppm, m, 7H. |
| 88 | 2,4-dichlorophenyl | —CH₃ | —C₃H₇ | cyclopropyl | 4-(SCH₃)phenyl | (CDCl₃)Base 0.3–0.9 ppm, m, 7H; 1.1–1.8 ppm, m, 3H; 2.13 ppm, s, 3H; 2.44 ppm, s, 3H; 3.1 ppm, m, 2H; 4.66 ppm, d, 1H; 7–7.4 ppm, m, 7H. |
| 89 | 2,4-dichlorophenyl | Br | —C₃H₇ | cyclopropyl | phenyl | (CDCl₃)Base 0.6–1.1 ppm, m, 7H; 1.3–2.0 ppm, m, 3H; 3.25 ppm, m, 2H; 4.81 ppm, d, 1H; 7.2–7.65 ppm, m, 8H. |
| 90 | 2,4-dichlorophenyl | I | —C₃H₇ | cyclopropyl | phenyl | (CDCl₃)Base 0.5–1.1 ppm, m, 7H; 1.3–2.0 ppm, m, 3H; 3.32 ppm, m, 2H; 4.80 ppm, d, 1H; 7.2–7.7 ppm, m, 8H. |

TABLE VII-continued

| EXAMPLE | R₁ | R₂ | R₃ | R₅ | R₆ | NMR SPECTRUM (SOLVENT) |
|---|---|---|---|---|---|---|
| 91 | 2-Cl, 4-I-phenyl | —CH₃ | —C₃H₇ | cyclopropyl | phenyl | (CDCl₃)Base 0.4–1.1 ppm, m, 7H; 1.3–1.95 ppm, m, 3H; 2.19 ppm, s, 3H; 3.25 ppm, m, 2H; 4.75 ppm, d, 1H; 7.1–7.9 ppm, m, 8H. |

PHARMACEUTICAL PREPARATION

Example 94

Hard gelatin capsules containing a 20 mg dose of 4-(2, 4-dichlorophenyl)-2-[N-(dicyclopropylmethyl)-N-propylamino]-5-methylthiazole sulphate.

| | |
|---|---|
| 4-(2,4-Dichlorophenyl)-2-[N-(dicyclopropylmethyl)-N-propylamino]-5-methylthiazole sulphate | 20 mg |
| Maize starch | 15 mg |
| Lactose | 25 mg |
| Talc | 5 mg | per No. 3 hard gelatin capsule

We claim:

1. A compound selected from the compounds of of the formula I:

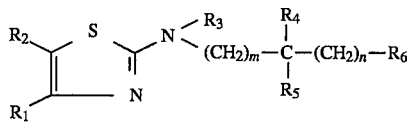

in which:

$R_1$ represents a radical of formula $A_1$ or a radical of formula $A_2$:

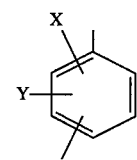

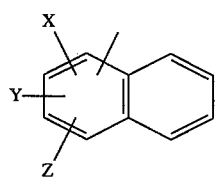

(in which formulae X, Y and Z, which may be identical or different, are selected from hydrogen, halogen, $(C_1-C_5)$alkoxy, $(C_1-C_5)$alkyl, hydroxyl, cyano, nitro, trifluoromethyl and $(C_7-C_9)$aralkyl), $R_2$ is selected from hydrogen, halogen, $(C_1-C_5)$alkyl, hydroxymethyl and formyl, $R_3$ is selected from $(C_1-C_5)$alkyl, $(C_3-C_8)$cycloalkyl, $(C_2-C_6)$alkenyl, $(C_4-C_8)$cycloalkylalkyl and phenyl, $R_4$ is selected from hydrogen, $(C_1-C_5)$alkyl, $(C_3-C_6)$cycloalkyl and $(C_4-C_8)$cycloalkylalkyl having a linear or branched chain, $R_5$ is selected from $(C_1-C_5)$alkyl, $(C_3-C_8)$cycloalkyl, optionally substituted with $(C_1-C_5)$alkyl, $(C_4-C_8)$cycloalkylalkyl having a linear or branched chain, $(C_2-C_6)$alkenyl, and a radical of the formula B:

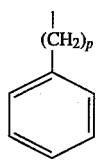

(in which formula p is equal to 0, 1, 2 or 3), $R_6$ is selected from phenyl, pyridyl, imidazolyl, pyrrolyl, thienyl and furyl (which are optionally substituted with one or more groups selected from halogen, $(C_1-C_5)$alkoxy, $(C_1-C_5)$alkyl, hydroxyl, cyano, nitro, trifluoromethyl, methylthio and radicals of formula B), and $(C_3-C_8)$cycloalkyl optionally substituted with $(C_1-C_5)$alkyl, m and n, which may be identical or different, each represent 0 or 1, their possible stereoisomers and their addition salts with an inorganic or organic acid.

2. A compound of formula I according to claim 1, in which:

$R_1$ represents a radical of formula $A_1$, $R_2$ is selected from halogen and $(C_1-C_5)$alkyl, $R_3$ is selected from $(C_1-C_5)$alkyl, $(C_3-C_8)$cycloalkyl, and $(C_2-C_6)$ alkenyl, $R_5$ is selected from $(C_1-C_5)$alkyl, $(C_3-C_8)$cycloalkyl optionally substituted with $(C_1-C_5)$alkyl and $(C_4-C_8)$cycloalkylalkyl having a linear or branched chain, $R_4$, $R_6$, m and n have the same meaning as for the formula I according to claim 1, their stereoisomers and also their addition salts with an inorganic or organic acid.

3. A compound of formula I according to claim 1, corresponding to the formula $I_A$:

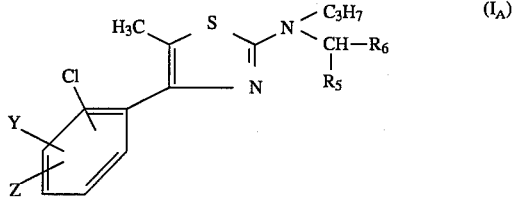

in which:

Y and Z have the same meaning as for the formula I according to claim 1, $R_5$ is selected from $(C_1-C_5)$alkyl and $(C_3-C_8)$cycloalkyl optionally substituted with $(C_1-C_5)$alkyl and $(C_4-C_8)$cycloalkylalkyl having a linear or branched chain, $R_6$ is selected from phenyl, pyridyl (optionally substituted with one or more groups selected from halogen, $(C_1-C_5)$alkoxy, $(C_1-C_5)$alkyl, hydroxyl, cyano, nitro, trifluoromethyl and methylthio), imidazolyl optionally substituted with a group selected from $(C_1-C_5)$alkyl and $(C_3-C_8)$cycloalkyl optionally substituted with $(C_1-C_5)$alkyl, their stereoisomers and their addition salts with an inorganic or organic acid.

4. 4-(2,4-dichlorophenyl)-5-methyl-2-{N-[cyclopropyl(4-pyridyl)methyl]-N-propylamino}thiazole, and its addition salts with an inorganic or organic acid.

5. 4-(2,4-dichlorophenyl)-5-methyl-2-[N-(α-cyclopropylbenzyl)-N-propylamino]thiazole, and its addition salts with an inorganic or organic acid.

6. 4-(2,4-dichlorophenyl)-5-methyl-2-[N-(dicyclopropylmethyl)-N-propylamino]thiazole, and its addition salts with an inorganic or organic acid.

7. 4-(2,4-dichlorophenyl)-5-methyl-2-{N-[cyclopentyl(cyclopropyl)methyl]-N-propylamino}thiazole, and its addition salts with an inorganic or organic acid.

8. 4-(2-chloro-4-methylphenyl)-5-methyl-2-[N-(dicyclopropylmethyl)-N-propylamino]thiazole, and its addition salts with an inorganic or organic acid.

9. Method of treatment of ailments necessitating a modulation of the action of corticotropin releasing factor (CRF) consisting in administering to a man in need thereof a therapeutically effective amount of a compound according to claim 1.

10. A pharmaceutical composition for the treatment of pathologies involving the corticotropin releasing factor containing an effective amount of a compound according to claim 1, in base form or in the form of a salt with a pharmaceutically acceptable inorganic or organic acid, and a pharmaceutically acceptable, non-toxic, inert excipient.

* * * * *